(12) United States Patent
Caroff et al.

(10) Patent No.: US 10,047,080 B2
(45) Date of Patent: Aug. 14, 2018

(54) (R)-2-METHYL-PIPERAZINE DERIVATIVES AS CXCR3 RECEPTOR MODULATORS

(71) Applicant: Idorsia Pharmaceuticals Ltd., Allschwil (CH)

(72) Inventors: Eva Caroff, Allschwil (CH); Emmanuel Meyer, Allschwil (CH)

(73) Assignee: IDORSIA PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 15/544,223

(22) PCT Filed: Jan. 14, 2016

(86) PCT No.: PCT/EP2016/050659
§ 371 (c)(1),
(2) Date: Jul. 17, 2017

(87) PCT Pub. No.: WO2016/113346
PCT Pub. Date: Jul. 21, 2016

(65) Prior Publication Data
US 2018/0009800 A1    Jan. 11, 2018

(30) Foreign Application Priority Data
Jan. 15, 2015 (WO) .................. PCT/EP2015/050691

(51) Int. Cl.
*C07D 417/14* (2006.01)

(52) U.S. Cl.
CPC .................................. *C07D 417/14* (2013.01)

(58) Field of Classification Search
CPC ...... C07D 417/14; A61P 29/00; A61K 31/427
See application file for complete search history.

(56) References Cited

U.S. PATENT DOCUMENTS

| | | |
|---|---|---|
| 7,589,199 B2 | 9/2009 | Pennell et al. |
| 7,645,755 B2 | 1/2010 | Illig et al. |
| 7,842,693 B2 | 11/2010 | Pennell et al. |
| 8,324,216 B2 | 12/2012 | Pennell et al. |
| 8,889,677 B2 | 11/2014 | Grauert et al. |
| 9,266,876 B2 | 2/2016 | Caroff et al. |
| 9,732,075 B2 | 8/2017 | Boss et al. |
| 9,850,256 B2 | 12/2017 | Cren et al. |
| 2004/0082571 A1 | 4/2004 | Pennell et al. |
| 2005/0256130 A1 | 11/2005 | Pennell et al. |
| 2006/0276465 A1 | 12/2006 | Kawahara et al. |
| 2008/0139572 A1 | 6/2008 | Wang et al. |
| 2010/0094006 A1 | 4/2010 | Nam et al. |
| 2011/0136823 A1 | 6/2011 | Deprez et al. |
| 2013/0072497 A1 | 3/2013 | Lorsbach et al. |
| 2014/0371204 A1 | 12/2014 | Caroff et al. |
| 2016/0176862 A1 | 6/2016 | Caroff et al. |
| 2017/0107214 A1 | 4/2017 | Caroff et al. |
| 2017/0305897 A1 | 10/2017 | Boss et al. |
| 2018/0009799 A1 | 1/2018 | Caroff et al. |
| 2018/0009800 A1 | 1/2018 | Caroff et al. |

FOREIGN PATENT DOCUMENTS

| | | |
|---|---|---|
| EP | 1 698 620 A1 | 9/2006 |
| WO | WO 2002/059107 A1 | 8/2002 |
| WO | WO 2002/059108 A1 | 8/2002 |
| WO | WO 2002/070511 A1 | 9/2002 |
| WO | WO 2005/003127 A1 | 1/2005 |
| WO | WO 2005/035534 A1 | 4/2005 |
| WO | WO 2005/040136 A1 | 5/2005 |
| WO | WO 2005/042516 A2 | 5/2005 |
| WO | WO 2005/044797 A1 | 5/2005 |
| WO | WO 2005/051304 A2 | 6/2005 |
| WO | WO 2006/047277 A2 | 5/2006 |

(Continued)

OTHER PUBLICATIONS

Office Action issued in U.S. Appl. No. 15/128,846 dated Sep. 14, 2017 (7 pages).
Groom, J. R. & Luster, A. D. Immunol Cell Biol 2011, 89, 207.
Groom, J. R. & Luster, A. D. Exp Cell Res 2011, 317, 620.
Lacotte, S., Brun, S., Muller, S. & Dumortier, H. Ann N Y Acad Sci 2009, 1173, 310.
Menke, J. et al. J Am Soc Nephrol 2008, 19, 1177.
Sakthivel, S. K. et al. J Immune Based Ther Vaccines 2008, 6, 6.
Mohan, K. & Issekutz, T. B. J Immunol 2007, 179, 8463.
Singh, U. P. et al. J Interferon Cytokine Res 2008, 28, 31.
Lammers, K. M. et al. Gastroenterology 2008, 135, 194.
Saetta, M. et al. Am J Respir Crit Care Med 2002, 165, 1404.

(Continued)

*Primary Examiner* — Erich A Leeser
(74) *Attorney, Agent, or Firm* — Arent Fox LLP

(57) ABSTRACT

The invention relates to compounds of Formula (I)

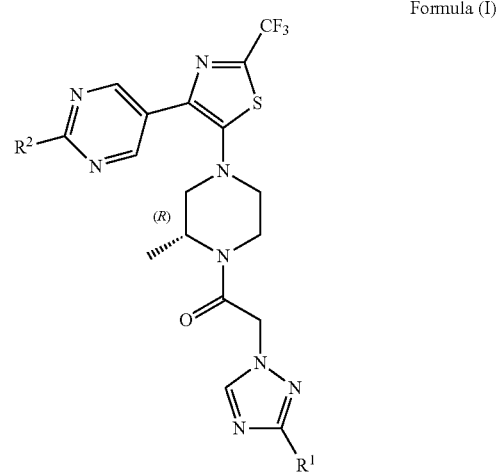

Formula (I)

wherein $R^1$ and $R^2$ are as described in the description; to pharmaceutically acceptable salts thereof, and to the use of such compounds as medicaments, especially as modulators of the CXCR3 receptor.

14 Claims, No Drawings

(56) References Cited

FOREIGN PATENT DOCUMENTS

| | | |
|---|---|---|
| WO | WO 2006/088836 A2 | 8/2006 |
| WO | WO 2006/088837 A2 | 8/2006 |
| WO | WO 2006/088840 A1 | 8/2006 |
| WO | WO 2006/088919 A2 | 8/2006 |
| WO | WO 2006/088920 A1 | 8/2006 |
| WO | WO 2006/088921 A2 | 8/2006 |
| WO | WO 2006/091428 A2 | 8/2006 |
| WO | WO 2007/002293 A2 | 1/2007 |
| WO | WO 2007/002742 A1 | 1/2007 |
| WO | WO 2007/014290 A2 | 2/2007 |
| WO | WO 2007/047202 A1 | 4/2007 |
| WO | WO 2007/048088 A2 | 4/2007 |
| WO | WO 2007/064553 A2 | 6/2007 |
| WO | WO 2007/070433 A2 | 6/2007 |
| WO | WO 2007/076318 A2 | 7/2007 |
| WO | WO 2007/100610 A2 | 9/2007 |
| WO | WO 2007/109238 A1 | 9/2007 |
| WO | WO 2007/124369 A2 | 11/2007 |
| WO | WO 2007/127635 A2 | 11/2007 |
| WO | WO 2008/003861 A1 | 1/2008 |
| WO | WO 2008/008453 A1 | 1/2008 |
| WO | WO 2008/013622 A2 | 1/2008 |
| WO | WO 2008/013925 A2 | 1/2008 |
| WO | WO 2008/079279 A1 | 7/2008 |
| WO | WO 2008/091580 A1 | 7/2008 |
| WO | WO 2008/091594 A2 | 7/2008 |
| WO | WO 2008/147822 A1 | 12/2008 |
| WO | WO 2009/020534 A2 | 2/2009 |
| WO | WO 2009/055514 A2 | 4/2009 |
| WO | WO 2009/079490 A1 | 6/2009 |
| WO | WO 2009/094407 A2 | 7/2009 |
| WO | WO 2009/094445 A2 | 7/2009 |
| WO | WO 2009/105435 A1 | 8/2009 |
| WO | WO 2009/132785 A1 | 11/2009 |
| WO | WO 2010/037479 A1 | 4/2010 |
| WO | WO 2010/065579 A2 | 6/2010 |
| WO | WO 2010/066353 A1 | 6/2010 |
| WO | WO 2010/126811 A1 | 11/2010 |
| WO | WO 2010/126851 A1 | 11/2010 |
| WO | WO 2010/149275 A1 | 12/2010 |
| WO | WO 2011/018401 A1 | 2/2011 |
| WO | WO 2011/018415 A2 | 2/2011 |
| WO | WO 2011/051243 A1 | 5/2011 |
| WO | WO 2011/051244 A1 | 5/2011 |
| WO | WO 2011/076699 A1 | 6/2011 |
| WO | WO 2011/084985 A1 | 7/2011 |
| WO | WO 2011/134969 A1 | 11/2011 |
| WO | WO 2011/144586 A1 | 11/2011 |
| WO | WO 2011/146182 A1 | 11/2011 |
| WO | WO 2011/147765 A1 | 12/2011 |
| WO | WO 2012/020060 A1 | 2/2012 |
| WO | WO 2012/025557 A1 | 3/2012 |
| WO | WO 2012/055837 A1 | 5/2012 |
| WO | WO 2012/069633 A1 | 5/2012 |
| WO | WO 2012/082580 A2 | 6/2012 |
| WO | WO 2012/104273 A1 | 8/2012 |
| WO | WO 2012/107475 A1 | 8/2012 |
| WO | WO 2012/107477 A1 | 8/2012 |
| WO | WO 2012/171337 A1 | 12/2012 |
| WO | WO 2013/037768 A1 | 3/2013 |
| WO | WO 2013/056911 A1 | 4/2013 |
| WO | WO 2013/056915 A1 | 4/2013 |
| WO | WO 2013/083741 A1 | 6/2013 |
| WO | WO 2013/107761 A1 | 7/2013 |
| WO | WO 2013/110134 A1 | 8/2013 |
| WO | WO 2013/114332 A1 | 8/2013 |
| WO | WO 2013/127784 A1 | 9/2013 |
| WO | WO 2013/127808 A1 | 9/2013 |
| WO | WO 2014/062938 A1 | 4/2014 |
| WO | WO 2014/075873 A1 | 5/2014 |
| WO | WO 2014/075874 A1 | 5/2014 |
| WO | WO 2014/092100 A1 | 6/2014 |
| WO | WO 2014/206896 A1 | 12/2014 |
| WO | WO 2015/011099 * 1/2015 | ........... C07D 417/14 |
| WO | WO 2015/011099 A1 | 1/2015 |
| WO | WO 2015/026683 A1 | 2/2015 |
| WO | WO 2015/145322 A1 | 10/2015 |
| WO | WO 2016/113344 A1 | 7/2016 |

OTHER PUBLICATIONS

Nie, L. et al. Respir Res 2008, 9, 82.
Mach, F. et al. J Clin Invest 1999, 104, 1041.
Veillard, N. R. et al. Circulation 2005, 112, 870.
Hancock, W. W. et al. J Exp Med 2000, 192, 1515.
Tacke, F., et al. Liver Int 2011, 31, 840.
Pradelli, E. et al. Int J Cancer 2009, 125, 2586.
Trentin, L. et al. J Clin Invest 1999, 104, 115.
van Weering, H. R. et al. Hippocampus 2011, 21, 220.
Reinhart, P. H. et al. Neurobiol Dis 2011, 43, 248.
A. Prokopowicz et al., Optimization of a biaryl series of CXCR3 antagonists, 244th ACS National Meeting, Philadelphia, US, Aug. 19-23, 2012.
Handbook of Pharmaceutical Salts. Properties, Selection and Use., P. Heinrich Stahl, Camille G. Wermuth (Eds.), Wiley-VCH, 2008.
Pharmaceutical Salts and Co-crystals', Johan Wouters and Luc Quéré (Eds.), RSC Publishing, 2012.
Remington, The Science and Practice of Pharmacy, 21st Edition (2005), Part 5, "Pharmaceutical Manufacturing" [published by Lippincott Williams & Wilkins].
Protective Groups in Organic Synthesis, T.W. Greene, P.G.M. Wuts, Wiley-Interscience, 1999.
Jenh et al., BMC Immunology 2012, 13:2.
Wang et al., Bioorg. Med. Chem. Lett. 2009, 114-118.
Watson et al., Bioorg. Med. Chem. Lett. 2007, 6806-6810.
Zhang et al., J. Med. Chem. 2013, 3996-4016.
Wijtmans et al., ChemMedChem 2008, 861-872.
McGuinness et al., Bioorg. Med. Chem. Lett. 2009 (doi: 10.1016/j.bmcl.2009.07.020).
A. Denoyer et al., 7 PLoS One, 1-11 (2012).
A. Fulton, 11 Current Oncology Reports, 125-131 (2009).
C. Billottet et al., 1836 Biochimica et Biophysica Acta, 287-295 (2013).
D. Jiang et al., 114 The Journal of Clinical Investigation, 291-299 (2004).
I.L. Stroke et al., 349 Biochemical and Biophysical Research Communications, 221-228 (2006).
M. Krauthausen et al., 125 The Journal of Clinical Investigation, 365-378 (2015).
S.V. Campanella et al., 105 PNAS, 4814-4819 (2008).
Y. Ha et al., 6 Cell Death and Disease, 1-11 (2015).

* cited by examiner

(R)-2-METHYL-PIPERAZINE DERIVATIVES AS CXCR3 RECEPTOR MODULATORS

CROSS-REFERENCE TO RELATED APPLICATIONS

This application is a National Stage entry of International Application No.: PCT/EP2016/050659, filed Jan. 14, 2016, which claims priority to International Application No. PCT/EP2015/050691, filed Jan. 15, 2015. The disclosure of the priority application is hereby incorporated in its entirety by reference.

The present invention relates to novel (R)-2-methyl-piperazine derivatives of Formula (I), and their use as pharmaceuticals. The invention also concerns related aspects including processes for the preparation of the compounds, pharmaceutical compositions containing one or more compounds of Formula (I), and especially their use as CXCR3 receptor modulators.

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

The chemokine receptor CXCR3 is a G-protein coupled receptor binding to the inflammatory chemokines CXCL9 (initially called MIG, monokine induced by interferon-γ [INF-γ]), CXCL10 (IP-10, INF-γ-inducible protein 10), and CXCL11 (I-TAC, INF-γ-inducible T cell α chemo-attractant). CXCR3 is mainly expressed on activated T helper type 1 (Th1) lymphocytes, but is also present on natural killer cells, macrophages, dendritic cells and a subset of B lymphocytes. The three CXCR3 ligands are expressed mainly under inflammatory conditions, expression in healthy tissue is very low. Cells that can express CXCR3 ligands, for instance after exposure to inflammatory cytokines such as interferon-γ or TNF-α, include diverse stromal cells such as endothelial cells, fibroblasts, epithelial cells, keratinocytes but also includes hematopoietic cells such as macrophages and monocytes. The interaction of CXCR3 and its ligands (henceforth referred to as the CXCR3 axis) is involved in guiding receptor bearing cells to specific locations in the body, particularly to sites of inflammation, immune injury and immune dysfunction and is also associated with tissue damage, the induction of apoptosis, cell growth, and angiostasis. CXCR3 and its ligands are upregulated and highly expressed in diverse pathological situations including autoimmune disorders, inflammation, infection, transplant rejection, fibrosis, neurodegeneration and cancer.

A role of the CXCR3 axis in autoimmune disorders is corroborated by several preclinical and clinical observations. Autoimmune disorders in which histological analysis of inflammatory lesions or serum levels of patients revealed elevated levels of CXCR3 ligands or increased numbers of CXCR3 positive cells include rheumatoid arthritis (RA), systemic lupus erythematosus (SLE), lupus nephritis, multiple sclerosis (MS), inflammatory bowel disease (IBD; comprising Crohn's disease and ulcerative colitis), and type I diabetes mellitus (Groom, J. R. & Luster, A. D. Immunol Cell Biol 2011, 89, 207; Groom, J. R. & Luster, A. D. Exp Cell Res 2011, 317, 620; Lacotte, S., Brun, S., Muller, S. & Dumortier, H. Ann N Y Acad Sci 2009, 1173, 310). As expression of CXCR3 ligands is very low in healthy tissue, the above cited correlative evidence strongly suggest a role for CXCR3 in human autoimmune diseases.

Preclinical disease models performed with CXCR3 deficient mice, mice deficient for one of the CXCR3 ligands or the use of antibodies blocking the function of either CXCR3 or one of its ligands further corroborate a role for the CXCR3 axis in immune pathology. For instance, it has been shown that mice deficient for either CXCR3 or the CXCR3 ligand CXCL9 show reduced pathology in a model for lupus nephritis (Menke, J. et al. J Am Soc Nephrol 2008, 19, 1177). In an animal model for another form of kidney inflammation, interstitial cystitis, administration of an antibody blocking CXCL10 function was shown to reduce pathology in cyclophosphamide-induced cystitis (Sakthivel, S. K. et al. J Immune Based Ther Vaccines 2008, 6, 6). Similarly, blocking CXCL10 with an antibody reduced pathology in a rat model of rheumatoid arthritis (Mohan, K. & Issekutz, T. B. J Immunol 2007, 179, 8463). Similarly, in a murine model of inflammatory bowel disease, a blocking antibody against CXCL10 could prevent pathology in a therapeutic setting (Singh, U. P. et J Interferon Cytokine Res 2008, 28, 31). Further, experiments performed with tissue from CXCR3 deficient mice suggests a role for CXCR3 in celiac disease, another autoimmune type disorder (Lammers, K. M. et al. Gastroenterology 2008, 135, 194).

Inflammatory diseases that are associated with an elevated expression of the CXCR3 axis include chronic obstructive pulmonary disorder (COPD), asthma, sarcoidosis, atherosclerosis and myocarditis (Groom, J. R. & Luster, A. D. Immunol Cell Biol 2011, 89, 207; Groom, J. R. & Luster, A. D. Exp Cell Res 2011, 317, 620).

One study has shown that CXCR3 positive cells are increased in the lungs of smokers with COPD compared to healthy subjects and immunoreactivity for the CXCR3-ligand CXCL10 was present in the bronchiolar epithelium of smokers with COPD but not in the bronchiolar epithelium of smoking and nonsmoking control subjects (Saetta, M. et al. Am J Respir Crit Care Med 2002, 165, 1404). These findings suggest that the CXCR3 axis may be involved in the immune cell recruitment that occurs in peripheral airways of smokers with COPD. In agreement with these observations, a preclinical study of COPD revealed an attenuation of acute lung inflammation induced by cigarette smoke in CXCR3 deficient mice (Nie, L. et al. Respir Res 2008, 9, 82).

In one investigation of atherosclerosis, CXCR3 expression was found on all T cells within human atherosclerotic lesions. CXCR3 ligands CXCL9, CXCL10 and CXCL11 were all found in endothelial and smooth muscle cells associated with those lesions, suggesting that they are involved in the recruitment and retention of CXCR3 positive cells, particularly activated T lymphocytes, observed within vascular wall lesions during atherogenesis (Mach, F. et al. J Clin Invest 1999, 104, 1041).

Preclinical studies further support a role of CXCR3 in the development of atherosclerosis. CXCR3 genetic deletion in mice lacking ApoE results in a significantly reduced atherosclerotic lesion development within abdominal aortas (Veillard, N. R. et al. Circulation 2005, 112, 870).

A pivotal role for the CXCR3 axis has also been suggested in rejection reactions after organ transplantation and bone marrow transplantation related toxicity (Groom, J. R. & Luster, A. D. Exp Cell Res 2011, 317, 620). Preclinically, CXCR3 deficient mice show a significant resistance to allograft rejection (Hancock, W. W. et al. J Exp Med 2000, 192, 1515). CXCR3 ligand plasma concentrations also positively correlate with diverse liver pathologies, including liver cirrhosis and fibrosis in humans (Tacke, F., et al. Liver Int 2011, 31, 840).

In the field of oncology, blocking the CXCR3 axis has been proposed to help limit the metastatic spread of cancer cells. For instance, administration of the small molecule CXCR3 receptor antagonist AMG487 could limit the metastasis of tumor cells to the lungs (Pradelli, E. et al. Int J Cancer 2009, 125, 2586). Functional evidence for a role of CXCR3 in regulating B-cell chronic lymphocytic leukemia (CLL) was reported by Trentin and coworkers (Trentin, L. et al. J Clin Invest 1999, 104, 115).

In the central nervous system, blocking the CXCR3 axis may have beneficial effects and prevent neurodegeneration. Increased expression of CXCL10 in the CNS has been demonstrated in ischemia, Alzheimer's disease, multiple sclerosis (MS), and human immunodeficiency virus (HIV)-encephalitis. For example, ex vivo experiments have shown that tissue derived from either CXCR3 or CXCL10 deficient mice, neuronal cell death was diminished after neurotoxic NMDA-treatment when compared to tissue derived from wild type mice (van Weering, H. R. et al. Hippocampus 2011, 21, 220). In a study looking to indentify drug-like molecules that provide neuroprotection against HTT fragment-induced neurodegeneration in a model for Huntington's disease, two CXCR3 receptor antagonists were identified (Reinhart, P. H. et al. Neurobiol Dis 2011, 43, 248.)

4-Thiazolyl-piperidine derivatives as CXCR3 receptor modulators have been disclosed in WO 2007/064553 and WO 2007/070433.

Different 1-(Piperazin-1-yl)-2-heteroaryl-ethanone derivatives as CXCR3 receptor modulators have been disclosed in WO 2007/100610, WO 2010/126811, WO 2013/114332, WO 2015/011099, WO 2015/145322 and on a poster presentation (A. Prokopowicz et al., *Optimization of a biaryl series of CXCR3 antagonists*, 244th ACS National Meeting, Philadelphia, US, Aug. 19-23, 2012).

It has now been found that (R)-2-methyl-piperazine derivatives of Formula (I) are potent CXCR3 modulators with a surprisingly improved profile in a hERG Q-Patch assay indicating a reduced risk of QT prolongation. These derivatives may be useful for the treatment of diseases that are mediated or sustained through the CXCR3 axis, including autoimmune disorders (e.g. rheumatoid arthritis, multiple sclerosis, inflammatory bowel disease, systemic lupus erythematosus, lupus nephritis, interstitial cystitis, celiac disease), inflammatory disorders (e.g. asthma, COPD, atherosclerosis, myocarditis, sarcoidosis), transplantation rejection, fibrosis (e.g. liver cirrhosis), neurodegeneration and conditions involving neuronal death (e.g. Alzheimer's disease, Huntington's disease), and cancer.

1) In a first embodiment, the present invention relates to compounds of Formula (I)

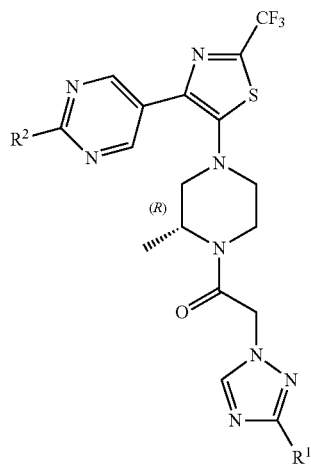

Formula (I)

wherein
R[1] represents $(C_{1-4})$alkyl, $(C_{1-2})$alkoxy-$(C_{1-2})$alkyl, hydroxy-$(C_{1-4})$alkyl or —C(O)NH$_2$; and
R[2] represents $(C_{3-6})$cycloalkyl, $(C_{1-4})$alkoxy, $(C_{3-6})$cycloalkoxy or $(C_{1-2})$fluoroalkyl;
and to the salts (in particular pharmaceutically acceptable salts) of such compounds.

For the avoidance of any doubt, the compounds of Formula (I) are (R)-configurated at the asymmetric carbon atom of the piperazine ring.

Definitions provided herein are intended to apply uniformly to the compounds of Formula (I) as defined in any one of embodiments 1) to 23), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The compounds of Formula (I) as defined in any one of embodiments 1) to 23), may contain one or more stereogenic or asymmetric centers, such as one or more asymmetric carbon atoms. The compounds of Formula (I) may thus be present as mixtures of stereoisomers or in stereoisomerically enriched form, preferably as pure stereoisomers. Mixtures of stereoisomers may be separated in a manner known to a person skilled in the art.

The term "enriched", for example when used in the context of enantiomers, is understood in the context of the present invention to mean especially that the respective enantiomer is present in a ratio (mutatis mutandis:purity) of at least 70:30, and notably of at least 90:10 (mutatis mutandis: purity of 70%/90%) with respect to the respective other enantiomer. Preferably the term refers to the respective essentially pure enantiomer. The term "essentially", for example when used in a term such as "essentially pure" is understood in the context of the present invention to mean especially that the respective stereoisomer/composition/compound etc. consists in an amount of at least 90, especially of at least 95, and notably of at least 99 percent by weight of the respective pure stereoisomer/composition/compound etc.

The term "alkyl", used alone or in combination, refers to a straight or branched saturated hydrocarbon chain containing one to four carbon atoms. The term "$(C_{x-y})$alkyl" (x and y each being an integer), refers to an alkyl group as defined before containing x to y carbon atoms. For example a $(C_{1-4})$alkyl group contains from one to four carbon atoms. Examples of $(C_{1-4})$alkyl groups are methyl, ethyl, n-propyl, iso-propyl, n-butyl, iso-butyl, sec.-butyl and tert.-butyl. Examples of $(C_{1-2})$alkyl groups are methyl and ethyl. In case $R^1$ represents "$(C_{1-4})$alkyl" the term means methyl, ethyl, n-propyl, iso-propyl, n-butyl, iso-butyl, sec.-butyl and tert.-butyl; preferably methyl, ethyl, n-propyl, iso-propyl and tert.-butyl; and more preferably ethyl and iso-propyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of $(C_{1-4})$alkoxy groups are methoxy, ethoxy, n-propoxy, iso-propoxy, n-butoxy, iso-butoxy, sec.-butoxy and tert.-butoxy. Examples of $(C_{1-2})$alkoxy groups are methoxy and ethoxy. In case $R^2$ represents "$(C_{1-4})$alkoxy" the term means methoxy, ethoxy, n-propoxy, iso-propoxy, n-butoxy, iso-butoxy, sec.-butoxy and tert.-butoxy and preferably ethoxy.

The term "hydroxy-$(C_{1-4})$alkyl", used alone or in combination, refers to an alkyl group as defined before containing from one to four carbon atoms in which one hydrogen atom has been replaced with hydroxy. Examples of said groups are hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxy-but-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl, and 2-hydroxy-1,1-dimethyl-eth-1-yl. In case "$R^1$" represents "hydroxy-$(C_{1-4})$alkyl" the term means hydroxy-methyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl, 2-hydroxy-prop-2-yl, 1-hydroxy-but-1-yl, 2-hydroxy-but-1-yl, 3-hydroxy-but-1-yl, 4-hydroxy-but-1-yl, 1-hydroxy-but-2-yl, 2-hydroxy-but-2-yl, 3-hydroxy-but-2-yl, 4-hydroxy-but-2-yl, 1-hydroxy-2-methyl-prop-1-yl, 2-hydroxy-2-methyl-prop-1-yl, 3-hydroxy-2-methyl-prop-1-yl, and 2-hydroxy-1,1-dimethyl-eth-1-yl. Preferred are hydroxy-methyl, 1-hydroxy-ethyl and 2-hydroxy-prop-2-yl and more preferred is 1-hydroxy-ethyl.

The term "$(C_{xa-ya})$alkoxy-$(C_{x-y})$alkyl" (x, xa, y and ya each being an integer) refers to an alkyl group as defined before containing x to y carbon atoms wherein one hydrogen atom has been replaced with $(C_{xa-ya})$alkoxy as defined before containing xa to ya carbon atoms. For example a "$(C_{1-2})$alkoxy-$(C_{1-2})$alkyl group" refers to an $(C_{1-2})$alkyl group as defined before containing one or two carbon atoms wherein one hydrogen atom has been replaced with $(C_{1-2})$alkoxy as defined before containing one or two carbon atoms. Examples of $(C_{1-2})$alkoxy-$(C_{1-2})$alkyl groups are methoxy-methyl, 1-methoxy-ethyl, 2-methoxy-ethyl, ethoxy-methyl, 1-ethoxy-ethyl and 2-ethoxy-ethyl. In case "$R^1$" represents "$(C_{1-2})$alkoxy-$(C_{1-2})$alkyl" the term means methoxy-methyl, 1-methoxy-ethyl, 2-methoxy-ethyl, ethoxy-methyl, 1-ethoxy-ethyl and 2-ethoxy-ethyl and preferably methoxy-methyl.

The term "fluoroalkyl" refers to an alkyl group as defined before containing one or two carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-2})$fluoroalkyl group contains one or two carbon atoms in which one to five hydrogen atoms have been replaced with fluorine. Representative examples of $(C_{1-2})$fluoroalkyl groups include fluoromethyl, difluoromethyl, trifluoromethyl, 1-fluoroethyl, 1,1-difluoroethyl, 2-fluoroethyl, 2,2-difluoroethyl, and 2,2,2-trifluoroethyl. In case $R^2$ represents "$(C_{1-2})$fluoroalkyl" the term means preferably fluoromethyl, difluoromethyl, trifluoromethyl, 1-fluoroethyl, 1,1-difluoroethyl, 2-fluoroethyl, 2,2-difluoroethyl, and 2,2,2-trifluoroethyl and more preferably trifluoromethyl.

The term "cycloalkyl", used alone or in combination, refers to a saturated carbocyclic ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of $(C_{3-6})$cycloalkyl groups are cyclopropyl, cyclobutyl, cyclopentyl, and cyclohexyl. In case "$R^2$" represents "$(C_{3-6})$cycloalkyl" the term means cyclopropyl, cyclobutyl, cyclopentyl and cyclohexyl and preferably cyclopropyl.

The term "cycloalkoxy", used alone or in combination, refers to a cycloalkyl-O— group wherein the cycloalkyl group is as defined before. The term "$(C_{x-y})$cycloalkoxy" (x and y each being an integer) refers to a cycloalkoxy group as defined before containing x to y carbon atoms. For example a $(C_{3-6})$cycloalkoxy group means a group of the formula $(C_{3-6})$cycloalkyl-O— in which the term "$(C_{3-6})$cycloalkyl" has the previously given significance. Examples of $(C_{3-6})$cycloalkoxy groups are cyclopropyloxy, cyclobutyloxy, cyclopentyloxy and cyclohexyloxy. In case $R^2$ represents "$(C_{3-6})$cycloalkoxy" the term means cyclopropyloxy, cyclobutyloxy, cyclopentyloxy and cyclohexyloxy and preferably cyclobutyloxy.

2) A further embodiment of the invention relates to compounds of Formula (I) according to embodiment 1), wherein
$R^1$ represents $(C_{1-4})$alkyl, $(C_{1-2})$alkoxy-$(C_{1-2})$alkyl or hydroxy-$(C_{1-4})$alkyl; and
$R^2$ represents $(C_{3-6})$cycloalkyl, $(C_{1-4})$alkoxy or $(C_{1-2})$fluoroalkyl;
and to the salts (in particular pharmaceutically acceptable salts) of such compounds.

3) A further embodiment of the invention relates to compounds of Formula (I) according to embodiment 1), wherein
$R^1$ represents $(C_{1-4})$alkyl; and
$R^2$ represents $(C_{3-6})$cycloalkyl, $(C_{1-4})$alkoxy or $(C_{1-2})$fluoroalkyl;
and to the salts (in particular pharmaceutically acceptable salts) of such compounds.

4) A further embodiment of the invention relates to compounds of Formula (I) according to embodiment 1), wherein
$R^1$ represents methyl, ethyl, n-propyl, iso-propyl, tert.-butyl, methoxy-methyl, hydroxy-methyl, 1-hydroxy-ethyl, 2-hydroxy-prop-2-yl or —C(O)NH$_2$; and
$R^2$ represents cyclopropyl, ethoxy, cyclobutyloxy or trifluoromethyl;
and to the salts (in particular pharmaceutically acceptable salts) of such compounds.

5) A further embodiment of the invention relates to compounds of Formula (I) according to embodiment 1), wherein R¹ represents ethyl, n-propyl, iso-propyl, tert.-butyl, methoxy-methyl or 1-hydroxy-ethyl; and
R² represents cyclopropyl, ethoxy or trifluoromethyl;
and to the salts (in particular pharmaceutically acceptable salts) of such compounds.

6) A further embodiment of the invention relates to compounds of Formula (I) according to embodiment 1), wherein
R¹ represents ethyl, n-propyl, iso-propyl or tert.-butyl; and
R² represents cyclopropyl, ethoxy or trifluoromethyl;
and to the salts (in particular pharmaceutically acceptable salts) of such compounds.

7) A further embodiment of the invention relates to compounds of Formula (I) according to embodiment 1), wherein
R¹ represents $(C_{1-4})$alkyl or $(C_{1-2})$alkoxy-$(C_{1-2})$alkyl; and
R² represents $(C_{3-6})$cycloalkyl;
and to the salts (in particular pharmaceutically acceptable salts) of such compounds.

8) A further embodiment of the invention relates to compounds of Formula (I) according to embodiment 1), wherein
R¹ represents ethyl, iso-propyl or tert.-butyl; and
R² represents cyclopropyl;
and to the salts (in particular pharmaceutically acceptable salts) of such compounds.

9) A further embodiment of the invention relates to compounds of Formula (I) according to embodiment 1), wherein
R¹ represents $(C_{1-4})$alkyl or $(C_{1-2})$alkoxy-$(C_{1-2})$alkyl; and
R² represents $(C_{1-4})$alkoxy;
and to the salts (in particular pharmaceutically acceptable salts) of such compounds.

10) A further embodiment of the invention relates to compounds of Formula (I) according to embodiment 1), wherein
R¹ represents ethyl, iso-propyl or tert.-butyl; and
R² represents ethoxy;
and to the salts (in particular pharmaceutically acceptable salts) of such compounds.

11) A further embodiment of the invention relates to compounds of Formula (I) according to embodiment 1), wherein
R¹ represents $(C_{1-4})$alkyl, $(C_{1-2})$alkoxy-$(C_{1-2})$alkyl, hydroxy-$(C_{1-4})$alkyl or —C(O)NH₂; and
R² represents $(C_{1-2})$fluoroalkyl;
and to the salts (in particular pharmaceutically acceptable salts) of such compounds.

12) A further embodiment of the invention relates to compounds of Formula (I) according to embodiment 1), wherein
R¹ represents methyl, ethyl, n-propyl, iso-propyl, tert.-butyl, methoxy-methyl, hydroxy-methyl, 1-hydroxy-ethyl, 2-hydroxy-prop-2-yl or —C(O)NH₂; and
R² represents trifluoromethyl;
and to the salts (in particular pharmaceutically acceptable salts) of such compounds.

13) A further embodiment of the invention relates to compounds of Formula (I) according to embodiment 1), wherein
R¹ represents ethyl, n-propyl, iso-propyl, tert.-butyl, methoxy-methyl or 1-hydroxy-ethyl; and
R² represents trifluoromethyl;
and to the salts (in particular pharmaceutically acceptable salts) of such compounds.

14) A further embodiment of the invention relates to compounds of Formula (I) according to any one of embodiments 1), 2), 7), 9) or 11), wherein
R¹ represents $(C_{1-4})$alkyl;
and to the salts (in particular pharmaceutically acceptable salts) of such compounds.

15) A further embodiment of the invention relates to compounds of Formula (I) according to any one of embodiments 1) to 5), 7), 9) or 11) to 13), wherein
R¹ represents ethyl, n-propyl, iso-propyl or tert.-butyl;
and to the salts (in particular pharmaceutically acceptable salts) of such compounds.

16) A further embodiment of the invention relates to compounds of Formula (I) according to any one of embodiments 1), 2), 7), 9) or 11), wherein
R¹ represents $(C_{1-2})$alkoxy-$(C_{1-2})$alkyl;
and to the salts (in particular pharmaceutically acceptable salts) of such compounds.

17) A further embodiment of the invention relates to compounds of Formula (I) according to any one of embodiments 1), 2) or 11), wherein
R¹ represents hydroxy-$(C_{1-4})$alkyl;
and to the salts (in particular pharmaceutically acceptable salts) of such compounds.

18) A further embodiment of the invention relates to compounds of Formula (I) according to any one of embodiments 1), 2), 3) or 14) to 17), wherein
R² represents $(C_{3-6})$cycloalkyl;
and to the salts (in particular pharmaceutically acceptable salts) of such compounds.

19) A further embodiment of the invention relates to compounds of Formula (I) according to any one of embodiments 1), 2), 3) or 14) to 17), wherein
R² represents $(C_{1-4})$alkoxy;
and to the salts (in particular pharmaceutically acceptable salts) of such compounds.

20) A further embodiment of the invention relates to compounds of Formula (I) according to any one of embodiments 1) or 14) to 17), wherein
R² represents $(C_{3-6})$cycloalkoxy;
and to the salts (in particular pharmaceutically acceptable salts) of such compounds.

21) A further embodiment of the invention relates to compounds of Formula (I) according to any one of embodiments 1), 2), 3) or 14) to 17), wherein
R² represents $(C_{1-2})$fluoroalkyl;
and to the salts (in particular pharmaceutically acceptable salts) of such compounds.

22) Examples of compounds of Formula (I) as defined in embodiment 1) are selected from the group consisting of:
1-{(R)-4-[4-(2-Ethoxy-pyrimidin-5-yl)-2-trifluoromethyl-thiazol-5-yl]-2-methyl-piperazin-1-yl}-2-(3-isopropyl-[1,2,4]triazol-1-yl)-ethanone;
1-{(R)-4-[4-(2-Ethoxy-pyrimidin-5-yl)-2-trifluoromethyl-thiazol-5-yl]-2-methyl-piperazin-1-yl}-2-(3-ethyl-[1,2,4]triazol-1-yl)-ethanone;
2-(3-tert-Butyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone;
1-{(R)-4-[4-(2-Ethoxy-pyrimidin-5-yl)-2-trifluoromethyl-thiazol-5-yl]-2-methyl-piperazin-1-yl}-2-(3-methoxymethyl-[1,2,4]triazol-1-yl)-ethanone;
1-(2-{(R)-2-Methyl-4-[2-trifluoromethyl-4-(2-trifluoromethyl-pyrimidin-5-yl)-thiazol-5-yl]-piperazin-1-yl}-2-oxo-ethyl)-1H-[1,2,4]triazole-3-carboxylic acid amide;

2-(3-Ethyl-[1,2,4]triazol-1-yl)-1-{(R)-2-methyl-4-[2-trifluoromethyl-4-(2-trifluoromethyl-pyrimidin-5-yl)-thiazol-5-yl]piperazin-1-yl}-ethanone;

2-(3-Isopropyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-(3-tert-Butyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-(3-Methoxymethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

2-(3-Hydroxymethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;

1-{(R)-2-Methyl-4-[2-trifluoromethyl-4-(2-trifluoromethyl-pyrimidin-5-yl)-thiazol-5-yl]-piperazin-1-yl}-2-(3-propyl-[1,2,4]triazol-1-yl)-ethanone;

2-[3-(1-Hydroxy-ethyl)-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone;

2-[3-(1-Hydroxy-1-methyl-ethyl)-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone;

1-{(R)-4-[4-(2-Cyclobutoxy-pyrimidin-5-yl)-2-trifluoromethyl-thiazol-5-yl]-2-methyl-piperazin-1-yl}-2-(3-isopropyl-[1,2,4]triazol-1-yl)-ethanone;

1-{(R)-4-[4-(2-Cyclopropyl-pyrimidin-5-yl)-2-trifluoromethyl-thiazol-5-yl]-2-methyl-piperazin-1-yl}-2-(3-ethyl-[1,2,4]triazol-1-yl)-ethanone;

1-{(R)-4-[4-(2-Cyclopropyl-pyrimidin-5-yl)-2-trifluoromethyl-thiazol-5-yl]-2-methyl-piperazin-1-yl}-2-(3-isopropyl-[1,2,4]triazol-1-yl)-ethanone;

2-(3-tert-Butyl-[1,2,4]triazol-1-yl)-1-{(R)-4-[4-(2-cyclopropyl-pyrimidin-5-yl)-2-trifluoromethyl-thiazol-5-yl]-2-methyl-piperazin-1-yl}-ethanone;

1-{(R)-4-[4-(2-Cyclopropyl-pyrimidin-5-yl)-2-trifluoromethyl-thiazol-5-yl]-2-methyl-piperazin-1-yl}-2-(3-methoxymethyl-[1,2,4]triazol-1-yl)-ethanone;

1-{(R)-4-[4-(2-Ethoxy-pyrimidin-5-yl)-2-trifluoromethyl-thiazol-5-yl]-2-methyl-piperazin-1-yl}-2-(3-methyl-[1,2,4]triazol-1-yl)-ethanone;

2-(3-Methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone; and 1-{(R)-4-[4-(2-Cyclopropyl-pyrimidin-5-yl)-2-trifluoromethyl-thiazol-5-yl]-2-methyl-piperazin-1-yl}-2-(3-methyl-[1,2,4]triazol-1-yl)-ethanone;

or salts (in particular pharmaceutically acceptable salts) of such compounds.

23) The invention, thus, relates to compounds of the Formula (I) as defined in embodiment 1), and to such compounds further limited by the characteristics of any one of embodiments 2) to 22), all under consideration of their respective dependencies; to pharmaceutically acceptable salts thereof; and to the use of such compounds as medicaments especially in the treatment of disorders relating to a dysfunction of the CXCR3 receptor or dysfunction of ligands signalling through CXCR3, such as especially autoimmune disorders, inflammatory diseases, infectious diseases, transplant rejection, fibrosis, neurodegenerative disorders and cancer. Especially the following embodiments relating to the compounds of formula (I) are thus possible and intended and herewith specifically disclosed in individualized form:

1, 2+1, 3+1, 4+1, 5+1, 6+1, 7+1, 8+1, 9+1, 10+1, 11+1, 12+1, 13+1, 14+1, 14+2+1, 14+7+1, 14+9+1, 14+11+1, 15+1, 15+2+1, 15+3+1, 15+4+1, 15+5+1, 15+7+1, 15+9+1, 15+11+1, 15+12+1, 15+13+1, 16+1, 16+2+1, 16+7+1, 16+9+1, 16+11+1, 17+1, 17+2+1, 17+11+1, 18+1, 18+2+1, 18+3+1, 18+14+1, 18+14+2+1, 18+14+7+1, 18+14+9+1, 18+14+11+1, 18+15+1, 18+15+2+1, 18+15+3+1, 18+15+4+1, 18+15+5+1, 18+15+7+1, 18+15+9+1, 18+15+11+1, 18+15+12+1, 18+15+13+1, 18+16+1, 18+16+2+1, 18+16+7+1, 18+16+9+1, 18+16+11+1, 18+17+1, 18+17+2+1, 18+17+11+1, 19+1, 19+2+1, 19+3+1, 19+14+1, 19+14+2+1, 19+14+7+1, 19+14+9+1, 19+14+11+1, 19+15+1, 19+15+2+1, 19+15+3+1, 19+15+4+1, 19+15+5+1, 19+15+7+1, 19+15+9+1, 19+15+11+1, 19+15+12+1, 19+15+13+1, 19+16+1, 19+16+2+1, 19+16+7+1, 19+16+9+1, 19+16+11+1, 19+17+1, 19+17+2+1, 19+17+11+1, 20+1, 20+14+1, 20+14+2+1, 20+14+7+1, 20+14+9+1, 20+14+11+1, 20+15+1, 20+15+2+1, 20+15+3+1, 20+15+4+1, 20+15+5+1, 20+15+7+1, 20+15+9+1, 20+15+11+1, 20+15+12+1, 20+15+13+1, 20+16+1, 20+16+2+1, 20+16+7+1, 20+16+9+1, 20+16+11+1, 20+17+1, 20+17+2+1, 20+17+11+1, 21+1, 21+2+1, 21+3+1, 21+14+1, 21+14+2+1, 21+14+7+1, 21+14+9+1, 21+14+11+1, 21+15+1, 21+15+2+1, 21+15+3+1, 21+15+4+1, 21+15+5+1, 21+15+7+1, 21+15+9+1, 21+15+11+1, 21+15+12+1, 21+15+13+1, 21+16+1, 21+16+2+1, 21+16+7+1, 21+16+9+1, 21+16+11+1, 21+17+1, 21+17+2+1, 21+17+11+1, 22+1, and 23+1;

in the list above the numbers refer to the embodiments according to their numbering provided hereinabove whereas "+" indicates the dependency from another embodiment. The different individualized embodiments are separated by commas. In other words, "14+2+1" for example refers to embodiment 14) depending on embodiment 2), depending on embodiment 1), i.e. embodiment "14+2+1" corresponds to the compounds of embodiment 1) further limited by the features of the embodiments 2) and 14).

Where the plural form is used for compounds, salts, pharmaceutical compositions, diseases or the like, this is intended to mean also a single compound, salt, pharmaceutical composition, disease or the like.

Any reference to a compound of Formula (I) as defined in any one of embodiments 1) to 23) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

The present invention also includes isotopically labelled, especially $^2$H (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially $^2$H (deuterium) labelled compounds of Formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

The compounds of formula (I) as defined in any one of embodiments 1) to 23) and their pharmaceutically acceptable salts can be used as medicaments, e.g. in the form of pharmaceutical compositions for enteral (such especially oral) or parenteral (including topical application or inhalation) administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of Formula (I) as defined in any one of embodiments 1) to 23).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as useful for the prevention or treatment of certain diseases, such compounds are likewise suitable for use in the preparation of a medicament for the prevention or treatment of said diseases.

Another aspect of the invention concerns a method for the prevention or the treatment of a disease or disorder as mentioned below in a patient comprising the administration to said patient of a pharmaceutically active amount of a compound of Formula (I) as defined in any one of embodiments 1) to 23) or a pharmaceutically acceptable salt thereof.

The compounds according to Formula (I) as defined in any one of embodiments 1) to 23), or pharmaceutically acceptable salts thereof, are useful for the prevention or treatment of disorders relating to a dysfunction of the CXCR3 receptor or dysfunction of ligands signalling through CXCR3.

Such disorders relating to a dysfunction of the CXCR3 receptor or its ligands are diseases or disorders where a modulator of a human CXCR3 receptor is required. The above mentioned disorders may in particular be defined as comprising autoimmune disorders, inflammatory diseases, infectious diseases, transplant rejection, fibrosis, neurodegenerative disorders and cancer.

Autoimmune disorders may be defined as comprising rheumatoid arthritis (RA); multiple sclerosis (MS); inflammatory bowel disease (IBD; comprising Crohn's disease and ulcerative colitis); systemic lupus erythematosus (SLE); psoriasis; psoriatic arthritis; lupus nephritis; interstitial cystitis; celiac disease; antiphospholipid syndrome; thyroiditis such as Hashimoto's thyroiditis; lymphocytic thyroiditis; myasthenia gravis; type I diabetes; uveitis; episcleritis; scleritis; Kawasaki's disease, uveo-retinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis.

Inflammatory diseases may be defined as comprising asthma; COPD; atherosclerosis; myocarditis; dry eye syndrome (comprising Sjögren's dry eye syndrome); myopathies (comprising inflammatory myopathies); sarcoidosis; pulmonary arterial hypertension, especially associated with sarcoidosis; and obesity.

Infectious diseases may be defined as comprising diseases mediated by various infectious agents and complications resulting therefrom; such as malaria, cerebral malaria, leprosy, tuberculosis, influenza, *toxoplasma gondii,* dengue, hepatitis B and C, herpes simplex, *leishmania, chlamydia trachomatis,* lyme disease, west nile virus.

Transplant rejection may be defined as comprising rejection of transplanted organs such as kidney, liver, heart, lung, pancreas, cornea, and skin; graft-versus-host diseases; and chronic allograft vasculopathy.

Fibrosis may be defined as comprising liver cirrhosis (comprising primary biliary cirrhosis (PBC) and autoimmune hepatitis), idiopathic pulmonary fibrosis, renal fibrosis, endomyocardial fibrosis, systemic sclerosis, and arthrofibrosis.

Neurodegenerative disorders may be defined as comprising neurodegeneration and conditions involving neuronal death such as multiple sclerosis (including relapsing remitting multiple sclerosis and progressive multiple sclerosis), Alzheimer's disease, Parkinson's disease, Huntington's chorea, HIV associated dementia, prion mediated neurodegeneration, epilepsy, stroke, cerebral ischemia, cerebral palsy, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, narcolepsy, glossopharyngeal neuralgia, mild cognitive decline, cognitive decline, spinal muscular atrophy, and cerebral malaria.

Cancer may be defined as comprising all sorts of cancers such as large intestine cancer, rectal cancer, breast cancer, lung cancer, non-small cell lung cancer, prostate cancer, esophagal cancer, stomach cancer, liver cancer, bile duct cancer, spleen cancer, kidney cancer, urinary bladder cancer, uterine cancer, ovarian cancer, cervical cancer, testicular cancer, thyroid cancer, pancreas cancer, brain tumor, blood tumor, basophil adenoma, prolactinoma, hyperprolactinemia, adenomas, endometrial cancer, colon cancer; chronic lymphocytic leukemia (CLL); and especially the metastatic spread of those cancers.

Especially, compounds of Formula (I) according to any one of embodiments 1) to 23), or pharmaceutically acceptable salts thereof, are suitable for the prevention or treatment of diseases selected from one, several or all of the following groups of diseases and disorders:
1) Autoimmune disorders selected from rheumatoid arthritis (RA); multiple sclerosis (MS); inflammatory bowel disease (IBD; comprising Crohn's disease and ulcerative colitis); systemic lupus erythematosus (SLE); psoriasis; lupus nephritis; and type I diabetes;
2) Inflammatory diseases selected from COPD; dry eye syndrome (comprising Sjögren's dry eye syndrome); myopathies (comprising inflammatory myopathies); and sarcoidosis;
3) Transplant rejection selected from graft-versus-host diseases;
4) Fibrosis selected from liver cirrhosis (comprising primary biliary cirrhosis (PBC) and autoimmune hepatitis); and
5) Neurodegenerative disorders selected from Guillain-Barré syndrome.

Preparation of Compounds of Formula (I)

A further aspect of the invention is a process for the preparation of compounds of Formula (I). Compounds according to Formula (I) of the present invention can be prepared from commercially available or well known starting materials according to the methods described in the experimental part; by analogous methods; or according to the general sequence of reactions outlined below, wherein $R^1$ and $R^2$ are as defined for Formula (I). Other abbreviations used herein are explicitly defined, or are as defined in the experimental section. In some instances the generic groups $R^1$ and $R^2$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. The compounds obtained may also be converted into salts, especially pharmaceutically acceptable salts thereof in a manner known per se.

General Preparation Routes:

Scheme 1

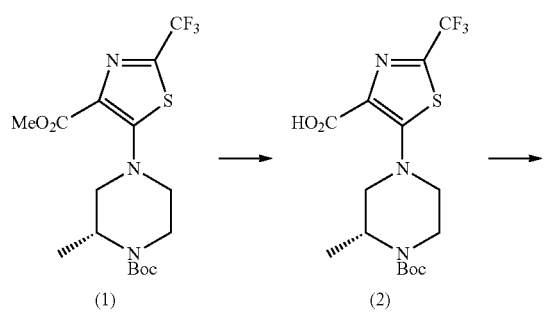

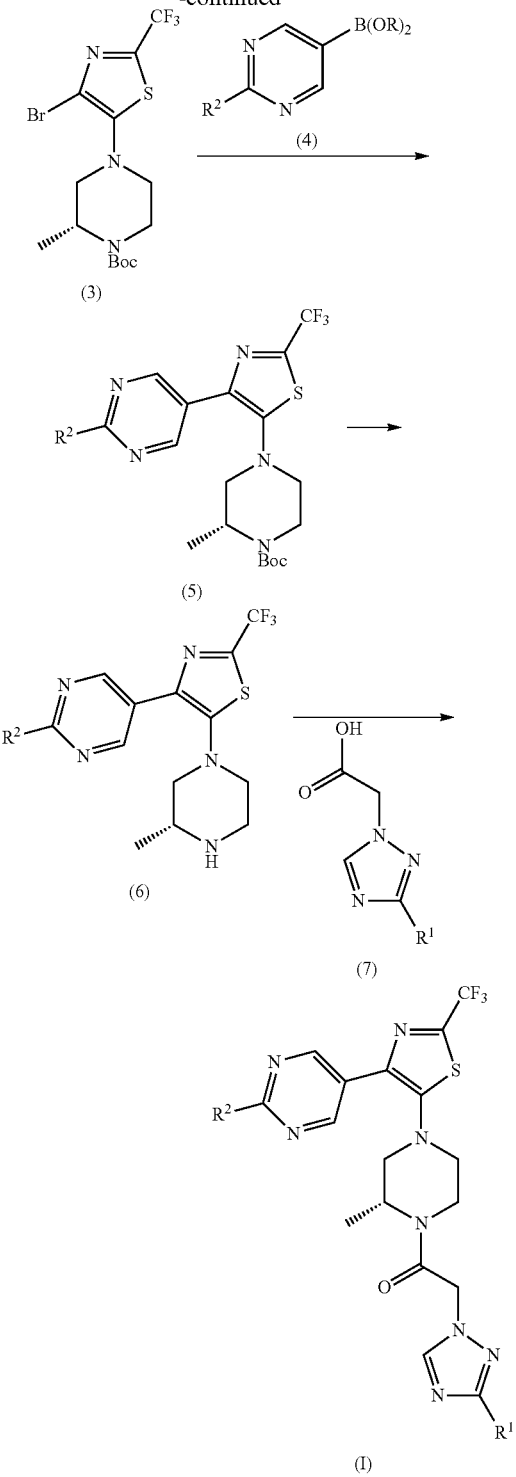

Compounds of Formula (I) can be prepared starting from intermediate (1), which is saponified under standard conditions (e.g. aq. NaOH in MeOH) to give compounds of structure (2) (Scheme 1). The carboxylic acid group in the compound of structure (2) is converted to the corresponding bromine (3) using (diacetoxyiodo)benzene and LiBr in THF at RT. Suzuki coupling can be performed using a coupling partner of structure (4), wherein R represents hydrogen or $(C_{1-4})$alkyl, using standard conditions for a Suzuki reaction, like using a suitable base such as aq. Na₂CO₃, a suitable palladium catalyst such as Pd(PPh₃)₂Cl₂, and a suitable solvent such as MeCN, preferably heating at a temperature around 80° C. The Boc protecting group of the obtained intermediate (5) can be subsequently cleaved under acidic conditions, preferably using HCl in a suitable solvent such as dioxane and at a temperature about RT to give the compound of structure (6). Compounds of Formula (I) can be obtained in a final step by an amide coupling with a carboxylic acid derivative (7) using standard peptide coupling methods such as HATU, in presence of a suitable base such as DIPEA or NEt₃ and in a suitable solvent such as DCM or DMF, preferably at a temperature about RT.

Scheme 2

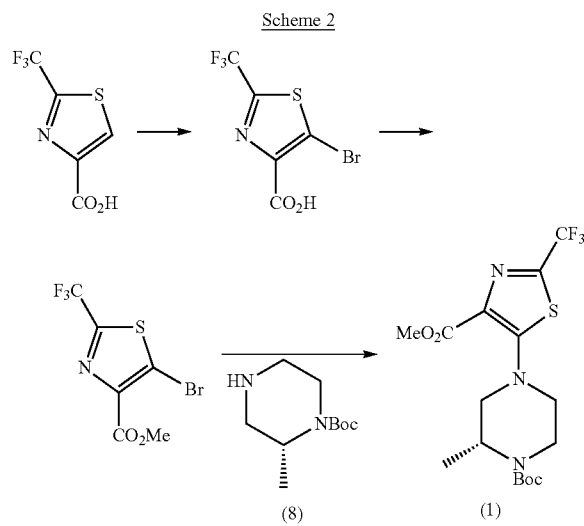

Compounds of structure (1) can be synthesized following the reaction sequence outlined in Scheme 2. Commercially available 2-(trifluoromethyl)thiazole-4-carboxylic acid is treated with n-butyl lithium and bromine in THF at a temperature around −78° C. The resulting brominated compound can be esterified using concentrated sulphuric acid in MeOH and heating at a temperature around 70° C. Nucleophilic aromatic substitution using commercially available piperazine derivative (8), in presence of a suitable base such as DIPEA, in a suitable solvent such as MeCN, and at a temperature around 80° C. provides compounds of structure (1).

The compounds of formula (7) are either commercially available, or can be synthesized following the route shown in Scheme 3.

Scheme 3

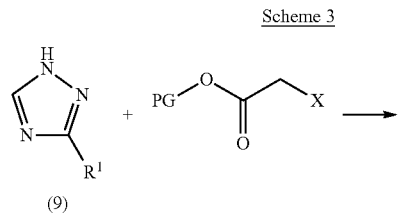

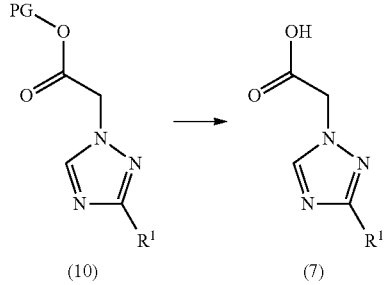

A triazole of structure (9) can be alkylated using an acetic acid derivative of formula X—CH₂—COO(PG), wherein X is a leaving group such as bromine and PG is a protecting group suitable for an acid function (e.g. benzyl), in presence of a base such as Cs₂CO₃, in a suitable solvent such as MeCN, and at a temperature around RT.

Deprotection of the intermediate (10), such as benzyl deprotection under H₂, using Pd/C as catalyst and EtOH as solvent at a temperature around RT, leads to the compound of structure (7). Other suitable acid function protecting groups and protection and deprotection methods are well known to one skilled in the art (see notably "Protective groups in organic synthesis", Greene T. W. and Wuts P. G. M., Wiley-Interscience, 1999).

The compounds of structure (4) are either commercially available or can be prepared in analogy to methods known to one skilled in the art such as the reaction of the respective 5-bromo-pyrimidine derivative with triisopropyl borate and n-BuLi in THF and toluene at a temperature around −78° C.

Compounds of Formula (I) may be obtained from other compounds of Formula (I) or their analogues by interconversion of a substituent in $R^1$-position to another substituent $R^1$. For instance, an analogue of Formula (I) wherein $R^1$ represents bromine may be transferred to a compound of Formula (I) wherein $R^1$ represents $(C_{2-4})$alkyl by (i) Suzuki reaction using the respective $(C_{2-4})$alkenylboronic acid ester derivative (e.g. isopropenylboronic acid pinacol ester) in the presence of a palladium catalyst such as Pd(PPh₃)₂Cl₂ and (ii) hydrogenation using for instance hydrogen in the presence of Pd/C in a solvent such as MeOH. A compound of Formula (I) wherein $R^1$ represents C(O)NH₂ may be prepared by hydrolysis of the respective nitrile using conc. H₂SO₄ in a solvent such as DCM. Further, a compound of Formula (I) wherein $R^1$ represents hydroxy-$(C_{1-4})$alkyl may be obtained from the respective compound wherein $R^1$ represents methoxy-$(C_{1-4})$alkyl by demethylation using BBr₃ in a solvent such as DCM or from the respective ketone wherein $R^1$ represents —C(O)—$(C_{1-3})$alkyl by reduction with NaBH₄.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase such as a Daicel ChiralPak IC (5 μm) column. Typical conditions of chiral HPLC are an isocratic mixture of eluent A (EtOH or iPrOH, in presence or absence of an amine such as NEt₃ or DEA) and eluent B (hexane or MeCN), at a flow rate of 0.8 to 16 mL/min.

EXPERIMENTAL SECTION

Abbreviations (as Used Herein and in the Description Above)

aq. aqueous
Boc tert.-butyloxycarbonyl

BSA Bovine serum albumine
Bu butyl
CC column chromatography on silica gel
CHO Chinese hamster ovary
CV column volume
DCM dichloromethane
DEA diethylamine
DIPEA N-ethyldiisopropylamine
DMF dimethylformamide
DMSO dimethylsulfoxide
EA ethyl acetate
EDTA ethylenediaminetetraacetic acid
EGTA ethylene glycol tetraacetic acid
Et ethyl
FBS fetal bovine serum
FLIPR Fluorescent imaging plate reader
Fluo-4-AM 2-{[2-(2-{5-[bis(carboxymethyl)amino]-2-methylphenoxy}ethoxy)-4-(2,7-difluoro-6-hydroxy-3-oxo-3H-xanthen-9-yl)phenyl](carboxymethyl)amino}acetic acid
G418 (2R,3S,4R,5R,6S)-5-amino-6-[(1R,2S,3S,4R,6S)-4,6-diamino-3-[(2R,3R,4R,5R)-3,5-dihydroxy-5-methyl-4-methylaminooxan-2-yl]oxy-2-hydroxycyclohexyl]oxy-2-(1-hydroxyethyl)oxane-3,4-diol
h hour(s)
HATU 2-(7-Aza-1H-benzotriazole-1-yl)-1,1,3,3-tetramethyluronium
Hep heptanes
HEPES 4-(2-hydroxyethyl)-piperazine-1-ethanesulfonic acid
HV High vacuum
HPLC high performance liquid chromatography
iPr iso-propyl
LC liquid chromatography
m multiplet
M molarity [mol L$^{-1}$]
Me methyl
MS mass spectrometry
min minute(s)
NMR nuclear magnetic resonance spectroscopy
org. organic
PBS Phosphate buffered saline
Pd/C palladium on carbon
PG protecting group
Ph phenyl
Prep preparative
rpm rotations per minute
RT room temperature
s singulet
sat. Saturated
TFA trifluoroacetic acid
THF tetrahydrofuran
TLC Thin layer chromatography
$t_R$ retention time
UPLC Ultra performance liquid chromatography
I. Chemistry The following examples illustrate the preparation of biologically active compounds of the invention but do not at all limit the scope thereof.

General: All temperatures are stated in degrees Celsius (° C.). Unless otherwise indicated, the reactions take place at RT under an argon atmosphere and are run in a flame dried round-bottomed flask equipped with a magnetic stir bar.

Characterization Methods Used:

The LC-MS retention times have been obtained using the following elution conditions:

I) LC-MS (A):

Zorbax SB-Aq, 3.5 µm, 4.6×50 mm column thermostated at 40° C. The two elution solvents were as follows: solvent A=water+0.04% TFA; solvent B=MeCN. The eluent flow rate was 4.5 mL/min and the characteristics of the eluting mixture proportion in function of the time t from start of the elution are summarized in the table below (a linear gradient being used between two consecutive time points):

| t (min) | 0 | 1.0 | 1.45 | 1.55 |
|---|---|---|---|---|
| Solvent A (%) | 95 | 5 | 5 | 95 |
| Solvent B (%) | 5 | 95 | 95 | 5 |

II) LC-MS (B):

Acquity UPLC CSH C18 1.7 µM 2.1×50 mm ID column from Waters, thermostated in the Acquity UPLC Column Manager (60° C.) was used. The two elution solvents were as follows: solvent A=water+0.05% formic acid; solvent B=MeCN+0.045% formic acid. The eluent flow rate was 1 mL/min and the characteristics of the eluting mixture proportion in function of the time t from start of the elution are summarized in the table below (a linear gradient being used between two consecutive time points):

| t (min) | 0 | 1.4 | 1.8 | 1.9 | 2.0 |
|---|---|---|---|---|---|
| Solvent A (%) | 98 | 5 | 2 | 2 | 98 |
| Solvent B (%) | 2 | 95 | 98 | 98 | 2 |

Compound purity and identity was further confirmed by NMR spectroscopy (Bruker Avance II 400 MHz Ultrashield™ or Bruker Ascend™ 500 equipped with a 5 mm DCH cryoprobe), 1H (400 MHz or 500 MHz), 19F (376 MHz). The chemical shifts are reported in parts per million (ppm) relative to tetramethylsilane (TMS) or trichlorofluoromethane, and multiplicities are given as s (singlet) or m (multiplet).

The purifications by preparative LC-MS have been performed using the conditions described hereafter.

I) Preparative LC-MS (I):

A X-Bridge column (Waters C18, 10 µm OBD, 30×75 mm) was used. The two elution solvents were as follows: solvent A=water+0.5% NH$_4$OH (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min) | 0 | 0.01 | 4.0 | 6.0 | 6.2 | 6.6 |
|---|---|---|---|---|---|---|
| Solvent A (%) | 80 | 80 | 5 | 5 | 80 | 80 |
| Solvent B (%) | 20 | 20 | 95 | 95 | 20 | 20 |

II) Preparative LC-MS (II):

X-Bridge column (Waters C18, 10 µm OBD, 30×75 mm) was used. The two elution solvents were as follows: solvent A=water+0.5% NH$_4$OH (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 3.5 | 6.0 | 6.2 | 6.6 |
|---------------|----|------|-----|-----|-----|-----|
| Solvent A (%) | 70 | 70   | 5   | 5   | 70  | 70  |
| Solvent B (%) | 30 | 30   | 95  | 95  | 30  | 30  |

III) Preparative LC-MS (III):

A X-Bridge column (Waters C18, 10 µm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 80 | 80   | 5   | 5   | 80  | 80  |
| Solvent B (%) | 20 | 20   | 95  | 95  | 20  | 20  |

IV) Preparative LC-MS (IV):

An Atlantis column (Waters T3, 10 µm OBD, 30×75 mm) was used. The two elution solvents were as follows: solvent A=water+0.5% formic acid; solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 80 | 80   | 5   | 5   | 80  | 80  |
| Solvent B (%) | 20 | 20   | 95  | 95  | 20  | 20  |

V) Preparative LC-MS (V):

A X-Bridge column (Waters C18, 10 µm OBD, 30×75 mm) was used. The two elution solvents were as follows: solvent A=water+0.5% $NH_4OH$ (25%); solvent B=MeCN. The eluent flow rate was 75 mL/min and the characteristics of the eluting mixture proportion in function of the time t from start of the elution are summarized in the tables below (a linear gradient being used between two consecutive time points):

| t (min)       | 0  | 0.01 | 4.0 | 6.0 | 6.2 | 6.6 |
|---------------|----|------|-----|-----|-----|-----|
| Solvent A (%) | 90 | 90   | 5   | 5   | 90  | 90  |
| Solvent B (%) | 10 | 10   | 95  | 95  | 10  | 10  |

Preparative Chiral HPLC Methods Used:

The purifications by preparative chiral HPLC have been performed using the conditions described hereafter.

I) Preparative Chiral HPLC (I):

A ChiralPak IB column (5 µm, 30×250 mm) was used. The elution solvent was Hep/EtOH 60/40, run for 9 min and at a flow rate of 40 mL/min.

II) Preparative Chiral HPLC (II):

A (R,R) Whelk-01 column (10 µm, 50×250 mm) was used. The elution solvent was Hep/EtOH 70/30, run for 16.3 min and at a flow rate of 100 mL/min.

III) Preparative Chiral HPLC (III):

A ChiralPak IB column (5 µm, 30×250 mm) was used. The elution solvent was Hep/EtOH 50/50, run for 8 min and at a flow rate of 34 mL/min.

IV) Preparative Chiral HPLC (IV):

A ChiralPak IB column (5 µm, 20×250 mm) was used. The elution solvent was Hep/EtOH 50/50, 0.1% DEA, run for 18.7 min and at a flow rate of 16 mL/min.

V) Preparative Chiral HPLC (V):

A ChiralPak IB column (5 µm, 30×250 mm) was used. The elution solvent was Hep/EtOH 70/30, run for 11.8 min and at a flow rate of 34 mL/min.

VI) Preparative Chiral HPLC (VI):

A ChiralPak OZ-H column (5 µm, 20×250 mm) was used. The elution solvent was Hep/EtOH 50/50, 0.1% DEA, run for 11 min and at a flow rate of 19 mL/min.

Example 1: 1-{(R)-4-[4-(2-Ethoxy-pyrimidin-5-yl)-2-trifluoromethyl-thiazol-5-yl]-2-methyl-piperazin-1-yl}-2-(3-isopropyl-[1,2,4]triazol-1-yl)-ethanone 1.1.
5-Bromo-2-trifluoromethyl-thiazole-4-carboxylic acid To a solution of 2-(trifluoromethyl)thiazole-4-carboxylic acid (3.2 g) in anhydrous THF (60 mL) under argon cooled down to −78° C. was added n-BuLi (1.6M in hexane, 21.3 mL) dropwise over 15 min so that the internal temperature did not rise above −60° C. A solution of $Br_2$ (0.92 mL) in cyclohexane (8 mL) was then added dropwise to keep the internal temperature below −60° C. The resulting mixture was stirred at −78° C. for 2 h and carefully quenched by addition of water (50 mL). Citric acid (10%) was added until pH=2 and the mixture was extracted with EA. The org. layers were washed with brine, dried ($MgSO_4$), filtered off and evaporated to dryness to afford 4.15 g of brown solid, used without further purification. LC-MS (A): $t_R$=0.67 min. F-NMR ($CD_3OD$): −63.57 ppm (s).

1.2.
5-Bromo-2-trifluoromethyl-thiazole-4-carboxylic acid methyl ester

To a solution of intermediate 1.1 (12 g), MeOH (130 mL) was added $H_2SO_4$ (96%, 6.5 mL) and the mixture was stirred at 70° C. for 3 h. After cooling down, the reaction mixture was quenched with sat. aq. $Na_2CO_3$ and the solvent partially evaporated off. The residue was diluted with DCM and washed with aq. sat. $Na_2CO_3$ (1×), water (1×) and brine (1×), and the aq. phases were extracted with DCM (2×). The combined org. layers were dried over $MgSO_4$, filtrated off, evaporated and dried under HV to afford 12 g of brown resin. LC-MS (A): $t_R$=0.83 min. F-NMR ($CD_3OD$): −63.59 ppm (s).

1.3. (R)-4-(4-Methoxycarbonyl-2-trifluoromethyl-thiazol-5-yl)-2-methyl-piperazine-1-carboxylic acid tert-butyl ester To a solution of intermediate 1.2 (10 g) in MeCN (250 mL) were added (R)-1-N-Boc-2-methylpiperazine (7.19 g) and DIPEA (8.85 mL) at RT. The reaction mixture was stirred at 80° C. for 43 h. After cooling down, the reaction mixture was diluted with EA and washed with water and brine. The aq. layers were extracted with EA. The combined org. layers were dried over $MgSO_4$, filtrated off and evaporated to dryness. The crude was purified by CC (Biotage, SNAP 340 g, solvent A: Hep; solvent B: EA; gradient in % B: 10 over 5CV, 10 to 30 over 5CV, 30 over 5CV) to afford 9.14 g of yellow resin. LC-MS (A): $t_R$=0.97 min; $[M+H]^+$: 410.0.

1.4. (R)-4-(4-Carboxy-2-trifluoromethyl-thiazol-5-yl)-2-methyl-piperazine-1-carboxylic Acid tert-butyl ester To a solution of intermediate 1.3 (4.25 g) in EtOH (40 mL) was added 1M NaOH (40 mL) at RT and the reaction mixture was stirred for 1 h 20. The solvent was evaporated off and the residue acidified to pH 2 by the addition of aq. citric acid (10%). The aq. layer was extracted with DCM (3×) and the combined org. layers were dried over $Na_2SO_4$ and concentrated to dryness to afford 4.1 g as orange solid. LC-MS (A): $t_R$=0.88 min; [M+H]$^+$: 395.9.

1.5. (R)-4-(4-Bromo-2-trifluoromethyl-thiazol-5-yl)-2-methyl-piperazine-1-carboxylic acid tert-butyl ester To a solution of intermediate 1.4 (10.17 g) in THF (210 mL) were added LiBr (2.26 g) and (diacetoxyiodo)benzene (8.45 g) at RT. The resulting suspension was stirred at RT for 1 h 30. The reaction mixture was diluted with $H_2O$ and extracted with DCM (3×). The combined org. layers were dried over $MgSO_4$, filtrated off and evaporated to dryness. The crude was purified by CC (Biotage, SNAP 340 g cartridge, solvent A: Hep; solvent B: EA; gradient in % B: 5 for 5CV, 5 to 10 over 3CV) to afford 9.63 g as yellow solid. LC-MS (A): $t_R$=1.04 min; [M+H]$^+$: 429.2.

1.6. (R)-4-[4-(2-Ethoxy-pyrimidin-5-yl)-2-trifluoromethyl-thiazol-5-yl]-2-methyl-piperazine-1-carboxylic acid tert-butyl ester A mixture of intermediate 1.5 (1.63 g), 2-ethoxypyrimidine-5-boronic acid (778 mg), Pd(PPh$_3$)$_2$Cl$_2$ (152 mg), 1M $Na_2CO_3$ (12 mL) in MeCN (12 mL) was vigorously stirred at 80° C. under argon overnight. The reaction mixture was allowed to cool down to RT, diluted with $H_2O$ and extracted with DCM (3×). The combined org. layers were dried over $MgSO_4$, filtrated off and evaporated to dryness. The crude was purified by CC (Biotage, SNAP 50 g cartridge, solvent A: Hep; solvent B: EA; gradient in % B: 10 for 5CV, 10 to 30 over 5CV, 30 for 3CV) to afford 1.35 g as pale yellow resin. LC-MS (A): $t_R$=1.04 min; [M+H]$^+$: 473.9.

1.7. 2-Ethoxy-5-[5-((R)-3-methyl-piperazin-1-yl)-2-trifluoromethyl-thiazol-4-yl]-pyrimidine To solution of intermediate 1.6 (1.32 g) in DCM (45 mL) was added TFA (4.28 mL) at RT. The resulting mixture was stirred at RT overnight. The reaction mixture was treated with 1M NaOH to pH=14 and extracted with DCM (3×). The combined org. layers were dried over $MgSO_4$, filtrated off, evaporated and dried at HV to afford 1.01 g as beige solid. LC-MS (A): $t_R$=0.64 min; [M+H]$^+$: 374.0.

1.8. (3-Bromo-[1,2,4]triazol-1-yl)-acetate, lithium salt

To a solution of ethyl (3-bromo-1H-1,2,4-triazole-1-yl) acetate (200 mg) in THF (0.75 mL) and EtOH (0.75 mL) was added $H_2O$ (0.5 mL) followed by 2M LiOH (0.47 mL). The reaction mixture was stirred at RT overnight, was evaporated off and the residue dried at HV to afford 201 mg as white solid. LC-MS (A): $t_R$=0.29 min; [M+H]$^+$: 205.9.

1.9. 2-(3-Bromo-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone A mixture of intermediate 1.7 (120 mg), intermediate 1.8 (76 mg), HATU (159 mg), and DIPEA (82 µL) in DCM (4 mL) and DMF (1 mL) was stirred at RT overnight. DCM was removed by evaporation and the crude purified by Prep LC-MS (IV) to afford 102 mg as white solid. LC-MS (A): $t_R$=0.9 min; [M+H]$^+$: 561.0.

1.10. 1-{(R)-4-[4-(2-Ethoxy-pyrimidin-5-yl)-2-trifluoromethyl-thiazol-5-yl]-2-methyl-piperazin-1-yl}-2-(3-isopropenyl-[1,2,4]triazol-1-yl)-ethanone A mixture of intermediate 1.9 (40 mg), isopropenylboronic acid pinacol ester (15.1 mg), Pd(PPh$_3$)$_2$Cl$_2$ (2.8 mg), 1M $Na_2CO_3$ (1 mL) in MeCN (1 mL) was vigorously stirred at 80° C. under argon for 2 h. The reaction mixture was allowed to cool down to RT and evaporated to dryness. The crude was purified by Prep LC-MS (I). LC-MS (A): $t_R$=0.9 min; [M+H]$^+$: 523.2.

1.11. 1-{(R)-4-[4-(2-Ethoxy-pyrimidin-5-yl)-2-trifluoromethyl-thiazol-5-yl]-2-methyl-piperazin-1-yl}-2-(3-isopropyl-[1,2,4]triazol-1-yl)-ethanone A flask containing intermediate 1.10 (g), Pd/C (1.5 mg) in MeOH (1 mL) was evacuated and backfilled with argon (3×), afterwards evacuated and backfilled with $H_2$ (3×) and the reaction mixture was stirred at RT overnight. The reaction mixture was filtered over a syringe filter and the filtrate was evaporated to dryness. The crude was purified by Prep LC-MS (IV) to afford 7 mg as white solid. LC-MS (B): $t_R$=1.11 min; [M+H]$^+$: 525.2.

Example 2: 1-{(R)-4-[4-(2-Ethoxy-pyrimidin-5-yl)-2-trifluoromethyl-thiazol-5-yl]-2-methyl-piperazin-1-yl}-2-(3-ethyl-[1,2,4]triazol-1-yl)-ethanone

2.1. (3-Ethyl-[1,2,4]triazol-1-yl)-acetic acid benzyl ester

To a solution of 3-ethyl-1H-1,2,4-triazole (2 g) in MeCN (125 mL) was added Cs$_2$CO$_3$ (6.37 g) followed by benzyl bromoacetate (3.23 mL). The reaction mixture was stirred at RT overnight and evaporated to dryness. The residue was taken up in EA and washed with water. The aq. layers were extracted with EA (2×) and the combined org. layers were dried over Na$_2$SO$_4$, filtered off and evaporated to dryness. The residue was purified by CC (Biotage, SNAP 100 g cartridge, solvent A: DCM; solvent B: DCM/MeOH 8:2; gradient in % B: 15 for 4CV, 15 to 100 over 4CV, 100 for 1CV) to afford 3.89 g as first eluting fraction (mixture of two triazole regioisomers) and 309 mg as second eluting fraction ((3-ethyl-[1,2,4]triazol-4-yl)-acetic acid benzyl ester). The mixture of regioisomers was purified by preparative chiral HPLC (I). First eluting fraction: (5-ethyl-[1,2,4]triazol-1-yl)-acetic acid benzyl ester: 1.39 g yellow oil. LC-MS (A): $t_R$=0.72 min; [M+H]$^+$: 246.2. Roesy signal seen between CH$_2$CH$_3$ at 2.72 ppm and CH$_2$CO$_2$ at 4.93 ppm.

Second eluting fraction: (3-ethyl-[1,2,4]triazol-1-yl)-acetic acid benzyl ester: 2.08 g yellow solid. LC-MS (A): $t_R$=0.71 min; [M+H]$^+$: 246.2. Roesy signal seen between CH at 8.08 ppm (triazole) and CH$_2$CO$_2$ at 4.96 ppm.

2.2. (3-Ethyl-[1,2,4]triazol-1-yl)-acetic acid

A flask containing (3-ethyl-[1,2,4]triazol-1-yl)-acetic acid benzyl ester from step 2.1 (2.06 g), Pd/C (445 mg) in EtOH (20 mL) was evacuated and backfilled with argon (3×), afterwards evacuated and backfilled with $H_2$ (3×) and the reaction mixture was stirred at RT for 9 h. The reaction mixture was filtered over a celite plug and the filtrate was evaporated to dryness to afford 1.27 g as white solid. LC-MS (A): $t_R$=0.25 min; $[M+H]^+$: 156.2.

2.3. 1-{(R)-4-[4-(2-Ethoxy-pyrimidin-5-yl)-2-trifluoromethyl-thiazol-5-yl]-2-methyl-piperazin-1-yl}-2-(3-ethyl-[1,2,4]triazol-1-yl)-ethanone A mixture of intermediate 1.7 (50 mg), intermediate 2.2 (21 mg), HATU (66 mg), and $NEt_3$ (284) in DCM (1.5 mL) was stirred at RT overnight. The reaction mixture was evaporated to dryness and the crude purified by Prep LC-MS (I) to afford 15 mg as white solid. LC-MS (B): $t_R$=1.05 min; $[M+H]^+$: 511.2.

Example 3: 2-(3-tert-Butyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone 3.1. (3-tert-Butyl-[1,2,4]triazol-1-yl)-acetic acid benzyl ester This compound was prepared using a method analogous to that of Example 2, step 2.1, 3-tert-butyl-1H-1,2,4-triazole replacing 3-ethyl-1H-1,2,4-triazole. The desired compound was obtained after CC as single regioisomer. LC-MS (A): $t_R$=0.73 min; $[M+H]^+$: 274.1.

3.2. (3-tert-Butyl-[1,2,4]triazol-1-yl)-acetic acid

This compound was prepared using a method analogous to that of Example 2, step 2.2, intermediate 3.1 replacing (3-ethyl-[1,2,4]triazol-1-yl)-acetic acid benzyl ester. LC-MS (A): $t_R$=0.36 min; $[M+H]^+$: 184.3.

3.3. 2-(3-tert-Butyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone This compound was prepared using a method analogous to that of Example 2 step 2.3, intermediate 3.2 replacing intermediates 2.2. The desired compound was purified by Prep LC-MS (IV). LC-MS (A): $t_R$=0.84 min; $[M+H]^+$: 539.1.

Example 4: 1-{(R)-4-[4-(2-Ethoxy-pyrimidin-5-yl)-2-trifluoromethyl-thiazol-5-yl]-2-methyl-piperazin-1-yl}-2-(3-methoxymethyl-[1,2,4]triazol-1-yl)-ethanone 4.1. (3-Methoxymethyl-[1,2,4]triazol-1-yl)-acetic acid benzyl ester This compound was prepared using a method analogous to that of Example 2, step 2.1, 3-(methoxymethyl)-1H-1,2,4-triazol replacing 3-ethyl-1H-1,2,4-triazole. The crude was purified by two CC (1. Biotage, SNAP 10 g cartridge, solvent A: DCM; solvent B: DCM/MeOH 8:2; gradient in % B: 5 for 7CV, 5 to 15 over 3CV, 15 for 3CV. 2. Biotage, SNAP 10 g cartridge, solvent A: DCM; solvent B: DCM/MeOH 8:2; gradient in % B: 5 for 5CV, 5 to 10 over 3CV, 10 for 3CV, 10 to 15 for 3 CV) to yield two regioisomers:

First eluting fraction: (5-methoxymethyl-[1,2,4]triazol-1-yl)-acetic acid benzyl ester: colourless oil. LC-MS (A): $t_R$=0.71 min; $[M+H]^+$: 262.2.

Second eluting fraction: (3-methoxymethyl-[1,2,4]triazol-1-yl)-acetic acid benzyl ester: colourless oil. LC-MS (A): $t_R$=0.67 min; $[M+H]^+$: 262.1. Roesy signal seen between CH (triazole) at 8.17 ppm and $NCH_2CO_2$ at 5.01 ppm.

4.2. (3-Methoxymethyl-[1,2,4]triazol-1-yl)-acetic acid

This compound was prepared using a method analogous to that of Example 2, step 2.2, (3-methoxymethyl-[1,2,4]triazol-1-yl)-acetic acid benzyl ester from step 4.1 replacing (3-ethyl-[1,2,4]triazol-1-yl)-acetic acid benzyl ester. LC-MS (A): $t_R$=0.24 min; $[M+H]^+$: 172.0.

4.3. 1-{(R)-4-[4-(2-Ethoxy-pyrimidin-5-yl)-2-trifluoromethyl-thiazol-5-yl]-2-methyl-piperazin-1-yl}-2-(3-methoxymethyl-[1,2,4]triazol-1-yl)-ethanone This compound was prepared using a method analogous to that of Example 2, step 2.3, intermediate 4.2 replacing intermediate 2.2. The desired compound was purified by Prep LC-MS (IV). LC-MS (B): $t_R$=1.02 min; $[M+H]^+$: 527.2.

Example 5: 1-(2-{(R)-2-Methyl-4-[2-trifluoromethyl-4-(2-trifluoromethyl-pyrimidin-5-yl)-thiazol-5-yl]-piperazin-1-yl}-2-oxo-ethyl)-1H-[1,2,4]triazole-3-carboxylic acid amide 5.1. (R)-2-Methyl-4-[2-trifluoromethyl-4-(2-trifluoromethyl-pyrimidin-5-yl)-thiazol-5-yl]-piperazine-1-carboxylic acid tert-butyl ester This compound was prepared using a method analogous to that of Example 1, step 1.6, 2-(trifluoromethyl)pyrimidine-5-yl-boronic acid replacing 2-ethoxypyrimidine-5-boronic acid. LC-MS (A): $t_R$=1.06 min; $[M+H]^+$: 497.9.

5.2. 5-[5-((R)-3-Methyl-piperazin-1-yl)-2-trifluoromethyl-thiazol-4-yl]-2-trifluoromethyl-pyrimidine, as hydrochloride Salt A mixture of intermediate 5.1 (2.3 g) in HCl (10.2 mL, 4M in dioxane) was stirred at RT for 3 h. The white suspension was filtrated, the filtrate washed with $Et_2O$ and dried under HV to give 1.6 g as white solid. LC-MS (A): $t_R$=0.72 min; $[M+H++CH_3CN]^+$: 438.9.

5.3. 1-(2-{(R)-2-Methyl-4-[2-trifluoromethyl-4-(2-trifluoromethyl-pyrimidin-5-yl)-thiazol-5-yl]-piperazin-1-yl}-2-oxo-ethyl)-1H-[1, 2, 4]triazole-3-carbonitrile This compound was prepared using a method analogous to that of Example 2, step 2.3, 2-(3-cyano-1H-1,2,4-triazol-1-yl)acetic acid replacing intermediate 2.2 and intermediate 5.2 replacing intermediate 1.7. The desired compound was purified by Prep LC-MS (IV). LC-MS (B): $t_R$=1.19 min; $[M+H]^+$: 532.1.

5.4. 1-(2-{(R)-2-Methyl-4-[2-trifluoromethyl-4-(2-trifluoromethyl-pyrimidin-5-yl)-thiazol-5-yl]-piperazin-1-yl}-2-oxo-ethyl)-1H-[1,2,4]triazole-3-carboxylic Acid amide To a solution of intermediate 5.3 (18 mg) in DCM (0.1 mL) was added conc. $H_2SO_4$ (0.1 mL), and the resulting emulsion was vigorously stirred for 4 h 15. The reaction mixture was added portionwise to a mixture of $NH_4OH$ (25%) and ice, and the aq. layer was extracted with DCM (5×). The combined org. layers were washed with brine, dried over $MgSO_4$, evaporated and dried at HV. Purification by Prep. TLC (DCM/MeOH 95:5) afforded 9 mg as white solid. LC-MS (A): $t_R$=0.82 min; $[M+H]^+$: 550.0.

Example 6: 2-(3-Ethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 2, step 2.3, intermediate 5.2 replacing intermediate 1.7. The desired compound was purified by Prep LC-MS (IV). LC-MS (A): $t_R$=0.89 min; $[M+H]^+$: 535.0.

Example 7: 2-(3-Isopropyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone

7.1. (3-Isopropyl-[1,2,4]triazol-1-yl)-acetic Acid benzyl ester and (5-Isopropyl-[1,2,4]triazol-1-yl)-acetic Acid benzyl ester These compounds were prepared using a method analogous to that of Example 3, step 3.1, 3-isopropyl-1H-1,2,4-triazole replacing 3-ethyl-1H-1,2,4-triazole. The mixture of regioisomers was purified by preparative chiral HPLC (II). First eluting fraction: (3-isopropyl-[1,2,4]triazol-1-yl)-acetic acid benzyl ester. LC-MS (A): $t_R$=0.76 min; $[M+H]^+$: 260.2. Roesy signal seen between $CH_2$ at 4.96 ppm and CH (triazole) at 8.08 ppm.
Second eluting fraction: (5-isopropyl-[1,2,4]triazol-1-yl)-acetic acid benzyl ester. LC-MS (A): $t_R$=0.76 min; $[M+H]^+$: 260.2. Roesy signal seen between $CH_2$ at 4.96 ppm and CH (isopropyl) at 2.97 ppm.

7.2. (3-Isopropyl-[1,2,4]triazol-1-yl)-acetic Acid and (5-Isopropyl-[1,2,4]triazol-1-yl)-acetic Acid (3-Isopropyl-[1,2,4]triazol-1-yl)-acetic acid was prepared using a method analogous to that of Example 2, step 2.2, (3-isopropyl-[1,2,4]triazol-1-yl)-acetic acid benzyl ester of step 7.1 replacing intermediate 2.1. LC-MS (A): $t_R$=0.30 min; $[M+H]^+$: 170.2.
Alternatively, the mixture of regioisomers from step 7.1 was used to give a mixture of (3-isopropyl-[1,2,4]triazol-1-yl)-acetic acid and (5-isopropyl-[1,2,4]triazol-1-yl)-acetic acid.

7.3. 2-(3-Isopropyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 2, step 2.3, intermediate 5.2 replacing intermediate 1.7 and the mixture of regioisomers in step 7.2 replacing intermediate 2.2. The desired compound was purified by Prep LC-MS (IV) followed by preparative chiral HPLC (VI). First eluting fraction of preparative chiral HPLC: 2-(3-isopropyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone. LC-MS (B): $t_R$=1.17 min; $[M+H]^+$: 549.2.

Example 8: 2-(3-tert-Butyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 2, step 2.3, intermediate 5.2 replacing intermediate 1.7 and intermediate 3.2 replacing intermediate 2.2. The desired compound was purified by Prep LC-MS (II). LC-MS (B): $t_R$=1.23 min; $[M+H]^+$: 563.2.

Example 9: 2-(3-Methoxymethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 2, step 2.3, intermediate 5.2 replacing intermediate 1.7 and intermediate 4.2 replacing intermediate 2.2. The desired compound was purified by Prep LC-MS (I). LC-MS (B): $t_R$=1.09 min; $[M+H]^+$: 551.2.

Example 10: 2-(3-Hydroxymethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone To solution of Example 9 (25 mg) in DCM (1 mL) was added at −30° C. $BBr_3$ (58 μL; 1M in DCM) under argon and the resulting suspension was stirred at 0° C. for 3 h. The reaction mixture was quenched with $H_2O$, diluted with aq. sat. $NaHCO_3$ and extracted with EA (3×). The combined org. layers were washed with brine, dried over $MgSO_4$, filtrated off and evaporated to dryness. Prep LC-MS (IV) gave 5 mg as white powder. LC-MS (A): $t_R$=0.81 min; $[M+H]^+$: 537.1.

Example 11: 1-{(R)-2-Methyl-4-[2-trifluoromethyl-4-(2-trifluoromethyl-pyrimidin-5-yl)-thiazol-5-yl]-piperazin-1-yl}-2-(3-propyl-[1,2,4]triazol-1-yl)-ethanone

11.1. (3-propyl-[1,2,4]triazol-1-yl)-acetic Acid benzyl ester

These compounds were prepared using a method analogous to that of Example 2, step 2.1, 3-propyl-1H-1,2,4-triazole replacing 3-ethyl-1H-1,2,4-triazole. The mixture of regioisomers was purified by preparative chiral HPLC (III). First eluting fraction: (5-propyl-[1,2,4]triazol-1-yl)-acetic acid benzyl ester. LC-MS (A): $t_R$=0.77 min; $[M+H]^+$: 260.1. Roesy signal seen between $CH_2CO_2$ at 4.95 ppm and $CH_2CH_2CH_3$ at 2.65 ppm.
Second eluting fraction: (3-propyl-[1,2,4]triazol-1-yl)-acetic acid benzyl ester. LC-MS (A): $t_R$=0.76 min; $[M+H]^+$: 260.1. Roesy signal seen between $CH_2CO_2$ at 4.96 ppm and CH (triazole) at 8.08 ppm.

11.2. (3-Propyl-[1,2,4]triazol-1-yl)-acetic Acid

These compounds were prepared using a method analogous to that of Example 2, step 2.2, (3-propyl-[1,2,4]triazol- 1-yl)-acetic acid benzyl ester of step 11.1 replacing intermediate 2.1. LC-MS (A): $t_R$=0.35 min; [M+H]$^+$: 170.4.

11.3. 1-{(R)-2-Methyl-4-[2-trifluoromethyl-4-(2-trifluoromethyl-pyrimidin-5-yl)-thiazol-5-yl]-piperazin-1-yl}-2-(3-propyl-[1,2,4]triazol-1-yl)-ethanone This compound was prepared using a method analogous to that of Example 2, step 2.3, intermediate 5.2 replacing intermediate 1.7 and intermediate 11.2 replacing intermediate 2.2. The desired compound was purified by Prep LC-MS (I). LC-MS (B): $t_R$=1.17 min; [M+H]$^+$: 548.9.

Example 12: 2-[3-(1-Hydroxy-ethyl)-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone 12.1. (3-Acetyl-[1,2,4]triazol-1-yl)-acetic Acid benzyl ester This compound was prepared using a method analogous to that of Example 2, step 2.1, 1-(1H-1,2,4-triazol-5-yl)ethanone replacing 3-ethyl-1H-1,2,4-triazole. The crude was purified by CC (Biotage, SNAP 10 g cartridge, solvent A: Hep; solvent B: EA; gradient in % B: 30 for 4CV, 30 to 70 over 4CV, 70 for 2CV, 70 to 100 over 2CV, 100 for 2CV) to give the desired triazole regioisomer as second fraction. LC-MS (A): $t_R$=0.7 min; [M+H]$^+$: 260.1. Roesy signal seen between CH (triazole) at 8.28 ppm and CH$_2$ at 5.1 ppm.

12.2. (3-Acetyl-[1,2,4]triazol-1-yl)-acetic Acid

This compound was prepared using a method analogous to that of Example 2, step 2.2, intermediate 12.1 replacing intermediate 2.1. LC-MS (A): $t_R$=0.25 min; [M+H]$^+$: 170.0.

12.3. 2-(3-Acetyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 2, step 2.3, intermediate 5.2 replacing intermediate 1.7 and intermediate 12.2 replacing intermediate 2.2. The desired compound was purified by Prep LC-MS (I). LC-MS (A): $t_R$=0.89 min; [M+H]$^+$: 549.0.

12.4. 2-[3-(1-Hydroxy-ethyl)-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone To pale yellow solution of intermediate 12.3 (40 mg) in THF (0.75 mL) and EtOH (0.25 mL) was added NaBH$_4$ (1.4 mg) at 0° C. under argon and the reaction mixture was stirred at 0° C. for 1 h 30. Then a second batch of NaBH$_4$ (0.7 mg) was added and the mixture further stirred for 2 h 20. The reaction mixture was evaporated to dryness, the residue was suspended in EA and aq. sat. NH$_4$Cl was added and stirring was allowed for 30 min at RT. The layers were separated and the org. layer was washed with 1× brine. The aq. layers were re-extracted with EA (2×). The combined org. layers were dried over MgSO$_4$, filtrated off and evaporated to dryness. Purification by Prep TLC (DCM/MeOH 95/5) gave 10 mg as white solid. LC-MS (A): $t_R$=0.82 min; [M+H]$^+$: 551.1.

Example 13: 2-[3-(1-Hydroxy-1-methyl-ethyl)-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone To a suspension of intermediate 12.3 (40 mg) in Et$_2$O (0.75 mL) was added MeMgBr (48 µL; 3M in Et$_2$O) at −20° C. and the resulting suspension was stirred at RT for 1 h 30. The reaction mixture was quenched by addition of aq. sat. NH$_4$Cl and the aq. layer was extracted with EA (3×). The combined org. layers were dried over MgSO$_4$, filtrated and evaporated to dryness. Purification by Prep LC-MS (IV) gave 7 mg as white powder. LC-MS (A): $t_R$=0.84 min; [M+H]$^+$: 565.1.

Example 14: 1-{(R)-4-[4-(2-Cyclobutoxy-pyrimidin-5-yl)-2-trifluoromethyl-thiazol-5-yl]-2-methyl-piperazin-1-yl}-2-(3-isopropyl-[1,2,4]triazol-1-yl)-ethanone 14.1. (R)-4-[4-(2-Cyclobutoxy-pyrimidin-5-yl)-2-trifluoromethyl-thiazol-5-yl]-2-methyl-piperazine-1-carboxylic Acid tert-butyl ester This compound was prepared using a method analogous to that of Example 1, step 1.6, 2-(cyclobutoxy)pyrimidine-5-boronic replacing 2-ethoxypyrimidine-5-boronic acid. The crude was purified by Prep LC-MS (II) instead of CC. LC-MS (A): $t_R$=1.08 min; [M+H]$^+$: 500.1.

14.2. 2-Cyclobutoxy-5-[5-((R)-3-methyl-piperazin-1-yl)-2-trifluoromethyl-thiazol-4-yl]-pyrimidine, as hydrochloride Salt This compound was prepared using a method analogous to that of Example 5, step 5.2, intermediate 14.1 replacing intermediate 5.1. LC-MS (A): $t_R$=0.71 min; [M+H]$^+$: 400.1.

14.3. 1-{(R)-4-[4-(2-Cyclobutoxy-pyrimidin-5-yl)-2-trifluoromethyl-thiazol-5-yl]-2-methyl-piperazin-1-yl}-2-(3-isopropyl-[1,2,4]triazol-1-yl)-ethanone This compound was prepared using a method analogous to that of Example 2, step 2.3, intermediate 14.2 replacing intermediate 1.7 and the regioisomeric mixture in step 7.2 replacing intermediate 2.2. The crude was purified by CC (DCM/MeOH 97:3) followed by Prep LC-MS (I) and Preparative chiral HPLC (IV).

Second eluting fraction (preparative chiral HPLC): 1-{(R)-4-[4-(2-cyclobutoxy-pyrimidin-5-yl)-2-trifluoromethyl-thiazol-5-yl]-2-methyl-piperazin-1-yl}-2-(3-isopropyl-[1,2,4]triazol-1-yl)-ethanone: LC-MS (B): $t_R$=1.21 min; [M+H]$^+$: 551.3. Roesy signal seen between CH$_2$ at 5.14-5.37 ppm and CH (triazole) at 8.36 ppm.

Example 15: 1-{(R)-4-[4-(2-Cyclopropyl-pyrimidin-5-yl)-2-trifluoromethyl-thiazol-5-yl]-2-methyl-piperazin-1-yl}-2-(3-ethyl-[1,2,4]triazol-1-yl)-ethanone 15.1. (R)-4-[4-(2-Cyclopropyl-pyrimidin-5-yl)-2-trifluoromethyl-thiazol-5-yl]-2-methyl-piperazine-1-carboxylic acid tert-butyl ester This compound was prepared using a method analogous to that of Example 1, step 1.6, 2-cyclopropyl-5-(4,4,5,5- tetramethyl-1,3,2-dioxaborolan-2-yl)pyrimidine replacing 2-ethoxypyrimidine-5-boronic acid. LC-MS (A): $t_R$=1.06 min; [M+H]$^+$: 470.3.

15.2. 2-Cyclopropyl-5-[5-((R)-3-methyl-piperazin-1-yl)-2-trifluoromethyl-thiazol-4-yl]-pyrimidine, as hydrochloride Salt This compound was prepared using a method analogous to that of Example 5, step 5.2, intermediate 15.1 replacing intermediate 5.1. LC-MS (A): $t_R$=0.6 min; [M+H]$^+$: 370.1.

15.3. 1-{(R)-4-[4-(2-Cyclopropyl-pyrimidin-5-yl)-2-trifluoromethyl-thiazol-5-yl]-2-methyl-piperazin-1-yl}-2-(3-ethyl-[1,2,4]triazol-1-yl)-ethanone This compound was prepared using a method analogous to that of Example 2, step 2.3, intermediate 15.2 replacing intermediate 1.7. The crude was purified by Prep LC-MS (IV). LC-MS (B): $t_R$=1.07 min; [M+H]$^+$: 507.2.

Example 16: 1-{(R)-4-[4-(2-Cyclopropyl-pyrimidin-5-yl)-2-trifluoromethyl-thiazol-5-yl]-2-methyl-piperazin-1-yl}-2-(3-isopropyl-[1,2,4]triazol-1-yl)-ethanone This compound was prepared using a method analogous to that of Example 2, step 2.3, intermediate 15.2 replacing intermediate 1.7 and (3-isopropyl-[1,2,4]triazol-1-yl)-acetic acid from step 7.2 replacing intermediate 2.2. The crude was purified by Prep LC-MS (IV). LC-MS (A): $t_R$=0.8 min; [M+H]$^+$: 521.2.

Example 17: 2-(3-tert-Butyl-[1,2,4]triazol-1-yl)-1-{(R)-4-[4-(2-cyclopropyl-pyrimidin-5-yl)-2-trifluoromethyl-thiazol-5-yl]-2-methyl-piperazin-1-yl}-ethanone This compound was prepared using a method analogous to that of Example 2, step 2.3, intermediate 15.2 replacing intermediate 1.7 and intermediate 3.2 replacing intermediate 2.2. The crude was purified by Prep LC-MS (IV). LC-MS (B): $t_R$=1.18 min; [M+H]$^+$: 535.2.

Example 18: 1-{(R)-4-[4-(2-Cyclopropyl-pyrimidin-5-yl)-2-trifluoromethyl-thiazol-5-yl]-2-methyl-piperazin-1-yl}-2-(3-methoxymethyl-[1,2,4]triazol-1-yl)-ethanone This compound was prepared using a method analogous to that of Example 2, step 2.3, intermediate 15.2 replacing intermediate 1.7 and intermediate 4.2 replacing intermediate 2.2. The crude was purified by Prep LC-MS (IV). LC-MS (A): $t_R$=0.75 min; [M+H]$^+$: 523.2.

Example 19: 1-{(R)-4-[4-(2-Ethoxy-pyrimidin-5-yl)-2-trifluoromethyl-thiazol-5-yl]-2-methyl-piperazin-1-yl}-2-(3-methyl-[1,2,4]triazol-1-yl)-ethanone

19.1. (3-Methyl-[1,2,4]triazol-1-yl)-acetic acid benzyl ester

This compound was prepared using a method analogous to that of Example 2, step 2.1, 3-methyl-1H-1,2,4-triazole replacing 3-ethyl-1H-1,2,4-triazole. The mixture of regioisomers was purified by preparative chiral HPLC (V). First eluting fraction: (5-methyl-[1,2,4]triazol-1-yl)-acetic acid benzyl ester. LC-MS (A): $t_R$=0.68 min; [M+H]$^+$: 232.16. $^1$H-NMR (CDCl$_3$): 7.83 (s, 1H); 7.40-7.33 (m, 5H); 5.23 (s, 2H); 4.93 (s, 2H); 2.43 (s, 3H). Roesy signal seen between CH$_2$CO$_2$ at 4.93 ppm and CH$_3$ at 2.43 ppm.

Second eluting fraction: (3-methyl-[1,2,4]triazol-1-yl)-acetic acid benzyl ester. LC-MS (A): $t_R$=0.67 min; [M+H]$^+$: 232.16. $^1$H-NMR (CDCl$_3$): 8.05 (s, 1H); 7.40-7.30 (m, 5H); 5.23 (s, 0.95H, CH$_2$); 4.93-4.88 (3 s, 2H); 2.42 (s, 3H). Roesy signal seen between CH (triazole) at 8.05 ppm and CH$_2$CO$_2$ at 4.93-4.88 ppm.

19.2. (3-Methyl-[1,2,4]triazol-1-yl)-acetic Acid

This compound was prepared using a method analogous to that of Example 2, step 2.2, (3-methyl-[1,2,4]triazol-1-yl)-acetic acid benzyl ester from step 19.1 replacing intermediate 2.1. LC-MS (A): $t_R$=0.18 min; [M+H]$^+$: 142.22.

19.3. 1-{(R)-4-[4-(2-Ethoxy-pyrimidin-5-yl)-2-trifluoromethyl-thiazol-5-yl]-2-methyl-piperazin-1-yl}-2-(3-methyl-[1,2,4]triazol-1-yl)-ethanone This compound was prepared using a method analogous to that of Example 2, step 2.3, intermediate 19.2 replacing intermediate 2.2. The crude was purified by Prep LC-MS (V). LC-MS (A): $t_R$=0.81 min; [M+H]$^+$: 497.1.

Example 20: 2-(3-Methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone This compound was prepared using a method analogous to that of Example 2, step 2.3, intermediate 5.2 replacing intermediate 1.7 and intermediate 19.2 replacing intermediate 2.2. DIPEA was used instead of NEt$_3$. The crude was purified by Prep LC-MS (III). LC-MS (A): $t_R$=0.87 min; [M+H]$^+$: 521.0.

Example 21: 1-{(R)-4-[4-(2-Cyclopropyl-pyrimidin-5-yl)-2-trifluoromethyl-thiazol-5-yl]-2-methyl-piperazin-1-yl}-2-(3-methyl-[1,2,4]triazol-1-yl)-ethanone This compound was prepared using a method analogous to that of Example 2, step 2.3, intermediate 15.2 replacing intermediate 1.7 and intermediate 19.2 replacing intermediate 2.2. The crude was purified by Prep LC-MS (V). LC-MS (A): $t_R$=0.81 min; [M+H]$^+$: 493.1.

II. Biological Assays
A) FLIPR Assay:

The bioactivity of compounds is tested in a fluorometric imaging plate reader (FLIPR: Molecular Devices) using engineered CHO-K1 cells expressing the human CXCR3A (GenBank: AY242128) coupled to a G protein (Galpha(16)). Cells are plated the day prior to bioassay in F12 medium supplemented with 10% FBS and G418 and hygromycin antibiotics to maintain recombinant selection. At the day of bioassay, cells are washed and dye loaded for one hour with Fluo-4-AM (Invitrogen) in Hanks Balanced Salt Solution (Invitrogen), buffered with 20 mM Hepes at pH 7.4 and sodium bicarbonate (0.038%), containing 5 mM probenecid. This buffer, but lacking the dye and containing probenecid at a concentration of 2.5 mM, is also used for washing steps (wash buffer); or lacking both dye and probenecid but supplemented with 0.1% BSA for compound dilution steps (dilution buffer). Cells are washed free of excess dye and 60 microliter of wash buffer is added. Stock solutions of test compounds are made up at a concentration of 10 mM in DMSO, and serially diluted in dilution buffer to concentrations required for inhibition dose response curves. After a 10 minute incubation period at 37° C., 10 microliters of each compound dilution are transferred from a compound plate to the plate containing the recombinant cells in the FLIPR instrument according to the manufacturer's instructions. Following basal readings, 10 microliter CXCL10 agonist at a concentration of 20 nM (from Peprotech) is added, again using the FLIPR instrument. Changes in fluorescence are monitored before and after addition of the test compounds. Emission peak values above base level after CXCL10 addition are exported after base line subtraction.

B) Receptor Internalization Assay (RIA):

Stock solutions of test compounds are made up at a concentration of 10 mM in DMSO, and serially diluted in PBS containing 0.5% BSA to concentrations required for inhibition dose response curves. Diluted compounds are then mixed with an equal volume of CXCL10 (Peprotech) diluted in PBS. Anticoagulated venous human whole blood is added to the mixture, which is then incubated in a $CO_2$ incubator at 37° C. to allow for ligand mediated receptor internalization (final CXCL10 concentration is 9 nM). After 30 min, the blood is mixed with fluorescently labeled CXCR3 and CD4 specific antibodies (Becton Dickinson) and incubated on ice for 10 minutes. Samples are then mixed with BD FACS Lysing Solution (Becton Dickinson) in order to eliminate red blood cells. After washing the cells with PBS containing 0.5% BSA, the samples are then analyzed in a flow cytometer (FACS Canto II, Becton Dickinson). For data analysis using FACSDiva software (Becton Dickinson), the mean fluorescence corresponding to CXCR3 cell surface expression was determined on CD4 positive cells.

The calculated $IC_{50}$ values may fluctuate depending on the daily assay performance. Fluctuations of this kind are known to those skilled in the art. In the case where $IC_{50}$ values have been determined several times for the same compound, mean values are given. Data for the FLIPR assay are shown in Table 1 and for the receptor internalization assay (RIA) in Table 2.

TABLE 1

| Example No | FLIPR: $IC_{50}$ (nM) |
| --- | --- |
| 1 | 2.3 |
| 2 | 1.6 |
| 3 | 1.0 |
| 4 | 13 |
| 5 | 12 |
| 6 | 2.0 |
| 7 | 1.3 |
| 8 | 1.6 |
| 9 | 2.7 |
| 10 | 5.2 |
| 11 | 4.4 |
| 12 | 0.9 |
| 13 | 3.2 |
| 14 | 1.2 |
| 15 | 2.5 |
| 16 | 0.7 |
| 17 | 4.6 |
| 18 | 3.1 |
| 19 | 1.8 |
| 20 | 1.6 |
| 21 | 5.2 |

TABLE 2

| Example No | RIA: $IC_{50}$ (nM) |
| --- | --- |
| 1 | 299 |
| 2 | 235 |
| 3 | 552 |
| 4 | 950 |
| 5 | 1710 |
| 6 | 148 |
| 7 | 174 |
| 8 | 349 |
| 9 | 606 |
| 10 | 809 |
| 11 | 221 |
| 12 | 564 |
| 13 | 830 |
| 14 | 459 |
| 15 | 190 |
| 16 | 524 |
| 17 | 679 |
| 18 | 1390 |
| 19 | 211 |
| 20 | 189 |
| 21 | 462 |

C) hERG Q-Patch Assay:

Compounds are evaluated for block of the hERG K channel using CHO cells stably expressing the hERG gene (accession number U04270, bSys, Witterswil, Switzerland) and the QPatch robotic platform (Sophion, Ballerup, Denmark) in single-cell mode at room temperature. Cells are grown in culture flasks at 37° C. in 5% $CO_2$, in culture medium (Ham's F-12 Nutrient Mixture, Invitrogen 21765-029) supplemented with 9% (v/v) fetal calf serum, 0.9% Penicillin/Streptomycin (10,000 U/mL, Invitrogen 15140148), 100 µg/mL Hygromycin B (Invitrogen 10687010). When the cells are ~80% confluent (every 2-3 days), they are either split for further culture or used for electrophysiology. For further culture, cells are detached with 0.25% Trypsin EDTA solution (Invitrogen 25200-056) and a fraction of the cells (10-30%) is reseeded in culture medium. For electrophysiology, on the experimental day, cells are detached with 0.25% Trypsin EDTA solution and all cells are suspended in suspension medium (293 SFM II, Invitrogen 11686-029) supplemented with 20 mM HEPES and 0.04 mg/mL Trypsin inhibitor. Cells are kept in suspension medium at 32-35° C. in the QPatch robot until use, at which time aliquots are transferred to the extracellular solution (in mM: NaCl 150; KCl 4; $CaCl_2$ 1.2; $MgCl_2$ 1; HEPES 10; pH 7.4 with NaOH) containing 0.3% v/v DMSO and applied to the test plates. K+ currents are measured with the patch-voltage-clamp technique in the whole-cell configuration with the internal solution (in mM: KCl, 140; NaCl, 10; $MgCl_2$, 1; HEPES, 10; EGTA, 5; pH=7.2 with KOH). Currents are low-pass filtered using the internal Bessel filter of the QPatch robot with a cut-off frequency of 2 kHz and are digitized at 10 kHz. $K^+$ tail currents are produced from a holding voltage of −80 mV by a 500-ms depolarization to +20 mV followed by a 500-ms repolarization to −40 mV; tail current amplitudes are measured at the end of the repolarization to −40 mV. The pulse pattern is repeated every 10 sec during the experiment, baseline $K^+$ current is measured after 3 min in extracellular solution, test-solution containing compound is then applied, and $K^+$ current in presence of compound is measured 3 minutes after application to the cells. The respective test-solution is prepared by (1) dissolving the test-compound in pure DMSO, (2) diluting this DMSO solution in extracellular solution, and (3) adding further DMSO, such that the final test-solution has a concentration of either 300 nM or 3000 nM of the test-compound and contains 0.3% v/v DMSO. Compound effects are quantified as % block by dividing the current in presence of compound by the baseline current; two or three experiments are performed for each compound and the final value represents the mean of the results of each experiment.

| Example No | concentration [nM] | % block | concentration [nM] | % block |
|---|---|---|---|---|
| 1 | 300 | 6 | 3000 | 20 |
| 2 | 300 | −2 | 3000 | 4 |
| 3 | 300 | 10 | 3000 | 20 |
| 4 | 300 | 5 | 3000 | 10 |
| 5 | 300 | 1 | 3000 | 5 |
| 6 | 300 | 5 | 3000 | 22 |
| 7 | 300 | 5 | 3000 | 24 |
| 8 | 300 | 4 | 3000 | 23 |
| 9 | 300 | 2 | 3000 | 11 |
| 10 | 300 | 6 | 3000 | 17 |
| 11 | 300 | 5 | 3000 | 30 |
| 12 | 300 | 0 | 3000 | 4 |
| 13 | 300 | 10 | 3000 | 21 |
| 14 | 300 | 4 | 3000 | 27 |
| 15 | 300 | 3 | 3000 | 27 |
| 16 | 300 | 1 | 3000 | 25 |
| 17 | 300 | 0 | 3000 | 23 |
| 18 | 300 | 10 | 3000 | 22 |
| 19 | 300 | 9 | 3000 | 14 |
| 20 | 300 | 2 | 3000 | 18 |
| 21 | 300 | 3 | 3000 | 17 |

The invention claimed is:

1. A compound of Formula (I)

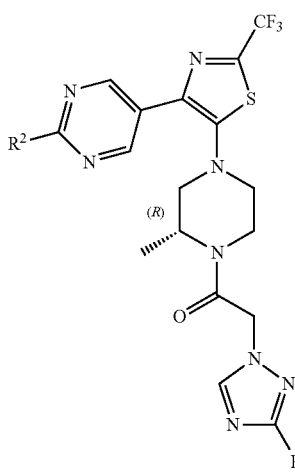

Formula (I)

wherein
$R^1$ represents $(C_{1-4})$alkyl, $(C_{1-2})$alkoxy-$(C_{1-2})$alkyl, hydroxy-$(C_{1-4})$alkyl or —C(O)NH$_2$; and
$R^2$ represents $(C_{3-6})$cycloalkyl, $(C_{1-4})$alkoxy, $(C_{3-6})$cycloalkoxy or $(C_{1-2})$fluoroalkyl;
or a salt thereof.

2. The compound according to claim 1, wherein
$R^1$ represents $(C_{1-4})$alkyl, $(C_{1-2})$alkoxy-$(C_{1-2})$alkyl or hydroxy-$(C_{1-4})$alkyl; and
$R^2$ represents $(C_{3-6})$cycloalkyl, $(C_{1-4})$alkoxy or $(C_{1-2})$fluoroalkyl;
or a salt thereof.

3. The compound according to claim 1, wherein
$R^1$ represents ethyl, n-propyl, iso-propyl, tert.-butyl, methoxy-methyl or 1-hydroxy-ethyl; and
$R^2$ represents cyclopropyl, ethoxy or trifluoromethyl;
or a salt thereof.

4. The compound according to claim 1, wherein
$R^1$ represents $(C_{1-4})$alkyl, $(C_{1-2})$alkoxy-$(C_{1-2})$alkyl, hydroxy-$(C_{1-4})$alkyl or —C(O)NH$_2$; and
$R^2$ represents $(C_{1-2})$fluoroalkyl;
or a salt thereof.

5. The compound according to claim 1, wherein $R^1$ represents $(C_{1-4})$alkyl; or a salt thereof.

6. The compound according to claim 1, wherein $R^1$ represents ethyl, n-propyl, iso-propyl or tert.-butyl; or a salt thereof.

7. The compound according to claim 1, wherein $R^2$ represents $(C_{3-6})$cycloalkyl; or a salt thereof.

8. The compound according to claim 1, wherein $R^2$ represents $(C_{1-4})$alkoxy; or a salt thereof.

9. The compound according to claim 1, wherein $R^2$ represents $(C_{1-2})$fluoroalkyl; or a salt thereof.

10. The compound according to claim 1, wherein the compound is:
1-{(R)-4-[4-(2-Ethoxy-pyrimidin-5-yl)-2-trifluoromethyl-thiazol-5-yl]-2-methyl-piperazin-1-yl}-2-(3-isopropyl-[1,2,4]triazol-1-yl)-ethanone;
1-{(R)-4-[4-(2-Ethoxy-pyrimidin-5-yl)-2-trifluoromethyl-thiazol-5-yl]-2-methyl-piperazin-1-yl}-2-(3-ethyl-[1,2,4]triazol-1-yl)-ethanone;
2-(3-tert-Butyl-[1,2,4]triazol-1-yl)-1-{(R)-4-[4-(2-ethoxy-pyrimidin-5-yl)-2-trifluoromethyl-thiazol-5-yl]-2-methyl-piperazin-1-yl}-ethanone;
1-{(R)-4-[4-(2-Ethoxy-pyrimidin-5-yl)-2-trifluoromethyl-thiazol-5-yl]-2-methyl-piperazin-1-yl}-2-(3-methoxymethyl-[1,2,4]triazol-1-yl)-ethanone;
1-(2-{(R)-2-Methyl-4-[2-trifluoromethyl-4-(2-trifluoromethyl-pyrimidin-5-yl)-thiazol-5-yl]-piperazin-1-yl}-2-oxo-ethyl)-1H-[1,2,4]triazole-3-carboxylic acid amide;
2-(3-Ethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
2-(3-Isopropyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
2-(3-tert-Butyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
2-(3-Methoxymethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
2-(3-Hydroxymethyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone;
1-{(R)-2-Methyl-4-[2-trifluoromethyl-4-(2-trifluoromethyl-pyrimidin-5-yl)-thiazol-5-yl]-piperazin-1-yl}-2-(3-propyl-[1,2,4]triazol-1-yl)-ethanone;
2-[3-(1-Hydroxy-ethyl)-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone;
2-[3-(1-Hydroxy-1-methyl-ethyl)-[1,2,4]triazol-1-yl]-1-{(R)-2-methyl-4-[2-trifluoromethyl-4-(2-trifluoromethyl-pyrimidin-5-yl)-thiazol-5-yl]-piperazin-1-yl}-ethanone;
1-{(R)-4-[4-(2-Cyclobutoxy-pyrimidin-5-yl)-2-trifluoromethyl-thiazol-5-yl]-2-methyl-piperazin-1-yl}-2-(3-isopropyl-[1,2,4]triazol-1-yl)-ethanone;

1-{(R)-4-[4-(2-Cyclopropyl-pyrimidin-5-yl)-2-trifluoromethyl-thiazol-5-yl]-2-methyl-piperazin-1-yl}-2-(3-ethyl-[1,2,4]triazol-1-yl)-ethanone;

1-{(R)-4-[4-(2-Cyclopropyl-pyrimidin-5-yl)-2-trifluoromethyl-thiazol-5-yl]-2-methyl-piperazin-1-yl}-2-(3-isopropyl-[1,2,4]triazol-1-yl)-ethanone;

2-(3-tert-Butyl-[1,2,4]triazol-1-yl)-1-{(R)-4-[4-(2-cyclopropyl-pyrimidin-5-yl)-2-trifluoromethyl-thiazol-5-yl]-2-methyl-piperazin-1-yl}-ethanone;

1-{(R)-4-[4-(2-Cyclopropyl-pyrimidin-5-yl)-2-trifluoromethyl-thiazol-5-yl]-2-methyl-piperazin-1-yl}-2-(3-methoxymethyl-[1,2,4]triazol-1-yl)-ethanone;

1-{(R)-4-[4-(2-Ethoxy-pyrimidin-5-yl)-2-trifluoromethyl-thiazol-5-yl]-2-methyl-piperazin-1-yl}-2-(3-methyl-[1,2,4]triazol-1-yl)-ethanone;

2-(3-Methyl-[1,2,4]triazol-1-yl)-1-{(R)-2-methyl-4-[2-trifluoromethyl-4-(2-trifluoromethyl-pyrimidin-5-yl)-thiazol-5-yl]-piperazin-1-yl}-ethanone; or 1-{(R)-4-[4-(2-Cyclopropyl-pyrimidin-5-yl)-2-trifluoromethyl-thiazol-5-yl]-2-methyl-piperazin-1-yl}-2-(3-methyl-[1,2,4]triazol-1-yl)-ethanone;

or a salt thereof.

11. A pharmaceutical composition comprising, as active principle, the compound according to claim 1, or a pharmaceutically acceptable salt thereof, and at least one therapeutically inert excipient.

12. The compound according to claim 1, or a pharmaceutically acceptable salt thereof, formulated as a medicament.

13. A method of treating a disease comprising administering to a patient in need thereof an effective amount of a compound according to claim 1, wherein the disease is an autoimmune disorder, an inflammatory disease, an infectious disease, a transplant rejection, fibrosis, a neurodegenerative disorder or a cancer.

14. A method of treating a disease comprising administering to a patient in need thereof an effective amount of a compound according to claim 11, wherein the disease is an autoimmune disorder, an inflammatory disease, an infectious disease, a transplant rejection, fibrosis, a neurodegenerative disorder or a cancer.

* * * * *